US007015212B1

(12) United States Patent
Neamati et al.

(10) Patent No.: US 7,015,212 B1
(45) Date of Patent: Mar. 21, 2006

(54) THIAZEPINE INHIBITORS OF HIV-1 INTEGRASE

(75) Inventors: Nouri Neamati, Fullerton, CA (US); Yves Pommier, Bethesda, MD (US); Antonio Garofalo, Siena (IT); Vito Nacci, Siena (IT)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 10/009,210

(22) PCT Filed: May 10, 2000

(86) PCT No.: PCT/US00/12847

§ 371 (c)(1),
(2), (4) Date: Nov. 9, 2001

(87) PCT Pub. No.: WO00/68235

PCT Pub. Date: Nov. 16, 2000

Related U.S. Application Data

(60) Provisional application No. 60/133,726, filed on May 12, 1999.

(51) Int. Cl.
  *C07D 513/04* (2006.01)
  *A61K 31/55* (2006.01)
  *A61P 31/18* (2006.01)
(52) U.S. Cl. .................... 514/211.04; 540/488
(58) Field of Classification Search .............. 540/488; 514/211.04
  See application file for complete search history.

(56) References Cited

U.S. PATENT DOCUMENTS

| 3,853,881 A | 12/1974 | Szmuszkovicz ............. 260/268 |
| 4,045,448 A | 8/1977 | Effland et al. ............. 260/326.5 |
| 4,263,207 A | 4/1981 | Rokach et al. ............. 260/239.3 |
| 4,287,203 A | 9/1981 | Suh et al. .................... 424/275 |
| 4,376,769 A | 3/1983 | Sherlock ..................... 424/246 |
| 4,592,866 A | 6/1986 | Cale, Jr. .................... 260/239.3 |
| 4,594,341 A | 6/1986 | Cheung et al. .............. 514/211 |
| 4,699,905 A | 10/1987 | Yanagisawa et al. ....... 514/211 |
| 4,778,790 A | 10/1988 | Yanagisawa et al. ....... 514/211 |
| 4,861,770 A | 8/1989 | Weiershausen et al. ..... 514/211 |
| 4,912,102 A | 3/1990 | Mohacsi et al. ............. 514/211 |
| 5,041,438 A | 8/1991 | Hsu ............................ 514/211 |
| 5,075,440 A | 12/1991 | Wustrow et al. ............. 540/468 |
| 5,141,735 A | 8/1992 | Bellemin et al. ............ 424/85.1 |
| 5,206,233 A | 4/1993 | Smith, III et al. ........... 514/211 |
| 5,270,464 A | 12/1993 | Kukla et al. ................. 540/556 |
| 5,334,591 A | 8/1994 | Baldwin et al. ............. 514/215 |
| 5,489,586 A | 2/1996 | Boschelli et al. ............ 514/211 |
| 5,504,077 A | 4/1996 | Collins et al. ............... 514/211 |
| 5,550,122 A | 8/1996 | Hargrave et al. ............ 514/211 |
| 5,571,806 A | 11/1996 | Hargrave et al. ............ 514/211 |
| 5,589,474 A | 12/1996 | Nicol et al. .................. 514/211 |
| 5,612,330 A | 3/1997 | Conner et al. ............... 514/211 |
| 5,719,140 A | 2/1998 | Chandrakumar et al. ... 514/211 |
| 5,786,353 A | 7/1998 | Albright et al. ............. 514/211 |
| 5,856,564 A | 1/1999 | Tanaka et al. ............... 562/457 |

FOREIGN PATENT DOCUMENTS

| EP | 0 135 803 A2 | 4/1985 |
| EP | 0 511 541 A1 | 11/1992 |
| WO | WO 94/10193 | 5/1994 |
| WO | WO 98/05657 | 2/1998 |
| WO | WO 98/18473 | 5/1998 |
| WO | WO 98/24804 | 6/1998 |

OTHER PUBLICATIONS

Neamati et al., "Design and discovery of HIV-1 integrase and inhibitors," *DDT*, vol. 2, No. 11, pp. 487-498 (1997).
Neamati et al., "Thiazolothiazepine Inhibitors of HIV-1 Integrase," *J. Med. Chem.*, vol. 42, pp. 3334-3341 (1999).
Archer et al., "Ring-Hydroxylated Analogues of Lucanthone as Antitumor Agents," *J. Med. Chem.*, vol. 25, No. 3, pp. 220-227 (1982).
Campiani et al., "Pyrrolobenzothiazepinones and Pyrrolobenzoxazepinones: Novel and Specific Non-Nucleoside HIV-1 Reverse Transcriptase Inhibitors with Antiviral Activity," *J. Med. Chem.*, vol. 39, No. 14, pp. 2672-2680 (1996).
Campiani et al., "New Antipsychotic Agents with Serotonin and Dopamine Antagonist Properties Based on a Pyrrolo[2,1-b][1,3]benzothiazepine Structure," *J. Med. Chem.*, vol. 41, No. 20, pp. 3763-3722 (1998).
Garofalo et al., "Polycondensed Heterocycles. V. Synthesis of 5H, 11H-Pyrrolo[2,1-c][1,4]Benzothiazepine," *Meterocycles*, vol. 31, No. 7, pp. 1291-1300 (1990).
Garofalo et al., "Polycondensed Heterocycles. VIII. Synthesis of 11-ARYL-5H,11H-Pyrrolo[2,1-c][1,4]Benzothiazepines by Pummerer Rearrangement-cyclization Reaction," *Meterocycles*, vol. 34, No. 1, pp. 51-60 (1992).

(Continued)

*Primary Examiner*—Bruck Kifle
(74) *Attorney, Agent, or Firm*—Klarquist Sparkman, LLP

(57) ABSTRACT

The present invention discloses non-catechol compounds, such as thiazolothiazepines, and analogs and derivatives thereof, which are anti-integrase inhibitors. The compounds, which are useful as treatments for HIV disease, include compounds (I), (II), (III), or pharmaceutically acceptable salts thereof wherein A is thiazole, benzene, naphthalene, pyridine, pyrimidine, pyrazine, or quinoline; R is one or more of H, halogen, lower alkyl, lower alkoxy, $NO_2$, lower ester or carboxylic acid; X—Y is $CH_2$—S, S—$CH_2$, $CH_2$—O, $CH_2$—S(O). S(O)—$CH_2$, $CH_2$—$CH_2$, $CH_2$—$CH_2$—$CH_2$, or $CH_2$—$CH_2$—$CH_2$—$CH_2$; $R_4$ is H or hydroxy; $R_5$ is H, phenyl, or alkylamine; W is S or O; and $R_6$ is H, substituted or unsubstituted alkyl or amine; and Z is S, O, $CH_2$, $CH_2CH_2$, or C=O.

22 Claims, 1 Drawing Sheet

OTHER PUBLICATIONS

Garofalo et al., "Benzothiazine and Benzothiazepine Derivatives: Synthesis and Preliminary Biological Evaluation," *Il Farmaco*, vol. 48, No. 2, pp. 275-283 (1993).

Garofalo et al., "Thianalogues of anti-tumor antibiotics. II. Synthesis and preliminary in vitro cytotoxicity evaluation of tricyclic [1,4]benzothiazepine derivatives," *Eur. J. Med. Chem.*, vol. 28, pp. 213-220 (1993).

Garofalo et al., "Polycondensed Heterocycles. IX. Pyrrolo[2,1-c][1,4]benzothiazepines. Synthesis of 3-(Dimethylamino)methyl Derivatives," *Tetrahedron*, vol. 52, No. 22, pp. 7745-7754 (1996).

Mohsen et al., "Synthesis and Anticonvulsant Properties of a Novel Series of 2-Substituted Amino-5-aryl-1,3,4-oxadiazole Derivatives," *J. Heterocyclic Chem.*, vol. 21, pp. 1415-1418 (1984).

Nacci et al., "Polycondensed Heterocycles. II. New Preparation Route to 11-Oxo-5H,11H-pyrrolo[2,1-c][1,4]benzothiazepine," *J. Heterocyclic Chem.*, vol. 23, pp. 769-773 (1986).

Nacci et al., "Thioanalogues of Antitumor Antibiotics," *Il Farmaco*, vol. 44, No. 4, pp. 423-433 (1989).

Neamati et al., "Design and discovery of HIV-1 integrase inhibitors," *Therapeutic Focus*, vol. 2, No. 11, pp. 487-498 (1997).

Neamati et al., "2-Mercaptobenzenesulphonamides as novel inhibitors of human immunodeficiency virus type 1 integrase and replication," *Antiviral Chemistry & Chemotherapy*, vol. 8, No. 6, pp. 485-495 (1997).

Effland et al., *J. Heterocycl. Chem* 22:1071-1075, 1985.

Nacci et al., *J. Heterocycl. Chem.* 25(3):1007-1013, 1988.

THIAZEPINE INHIBITORS OF HIV-1 INTEGRASE

PRIORITY CLAIM

This is a § 371 U.S. national stage of PCT/US00/12847 filed May 10, 2000, which was published in English under PCT Article 21(2), which in turn claims the benefit of U.S. Provisional Application 60/133,726 filed May 12, 1999.

FIELD OF THE INVENTION

The present invention concerns anti-retroviral drugs, and particularly prophylactic and therapeutic treatments for infections with the human immunodeficiency virus (HIV).

BACKGROUND OF THE INVENTION

HIV is a retrovirus that causes immunosuppression in humans (HIV disease), and leads to a disease complex known as the acquired immunodeficiency syndrome (AIDS). HIV disease is characterized by progressive functional deterioration of the immune system. The treatment of HIV disease has been significantly advanced by the recognition that combining different drugs with specific activities against different biochemical functions of the virus can help reduce the rapid development of drug resistant viruses that were seen in response to single drug treatment. However, even with combined treatments, multi-drug resistant strains of the virus have emerged. There is therefore a continuing need for the development of new anti-retroviral drugs that act specifically at different steps of the viral infection and replication cycle.

The integrase (IN) enzyme is an example of such a specific target. This enzyme catalyzes the insertion by virally-encoded integrase of proviral DNA into the host cell genome, which is the mechanism by which HIV and other retroviruses are introduced into human T-lymphoid cells. For HIV-1, this process is mediated by a 32 kD virally encoded integrase, having conserved sequences in the HIV long terminal repeats (LTR)[1]. Following reverse-transcription in the cytoplasm of infected cells, integrase cleaves two nucleotides from each of the viral DNA ends which contain a highly conserved CA motif. The cleaved DNA migrates to the nucleus as a part of a large nucleoprotein complex, where the integrase catalyzes the insertion of viral DNA into a host chromosome by a direct transesterification reaction.

In vitro assays have previously been developed to identify integrase inhibitors,[2,3] and have permitted the discovery of diverse classes of drugs that inhibit integrase.[5,6] However, the drugs discovered by these assays have not been highly selective and potent inhibitors of the integrase enzyme. Many of these drugs have additionally been non-selective inhibitors of reverse transcriptase or HIV protease, which limits their usefulness in combination therapy directed to different specific steps of the retroviral life cycle.

One class of reported integrase inhibitors is catechol-containing hydroxylated aromatics, which are non-selective integrase inhibitors that can also cross-link proteins[6] and chelate metals[7]. Non-catechol containing compounds, however, have been found to be cytotoxic, perhaps because they are unable to form reactive quinones. Such generalized cytotoxicity is a disadvantage, because it can affect host cells without being selective for retroviral eradication or inhibition.

Some hydrazides have been reported to be novel noncatechol-containing inhibitors of integrase. Structure-activity relationship studies among these inhibitors have indicated that the salicyl moiety is required for activity. Some benzothiazepine derivatives (such as diltiazem) have been reported to have lymphocyte protectant activity in U.S. Pat. No. 4,861,770, and benzodiazepine hydrazide derivatives have been reported to inhibit HIV integrase in WO 98/18473. However, a specific anti-integrase inhibitor with minimal cytotoxic activity is not yet available.

SUMMARY OF THE INVENTION

It has now surprisingly been found that certain noncatechol-containing compounds, including thiazepines, and particularly thiazolothiazepines, and analogs and derivatives thereof, are effective and selective anti-integrase inhibitors. The compounds of the present invention have particularly been found to inhibit both viral replication, and the activity of purified human immunodeficiency virus type-1 integrase (HIV-1 IN). Structure-activity studies have shown that the compounds possessing the pentatomic moiety SC(O)CNC(O) with two keto groups are in general more potent against purified IN than those containing only one keto group. Inhibitory potency against purified IN is maintained when the compounds are substituted with electron-donating or electron-withdrawing groups. Compounds with a naphthalene ring showed enhanced potency, as did those with thiazolo rings. Extension of the thiazole ring diminishes but did not eliminate potency.

The invention therefore includes a method of inhibiting a HIV integrase by exposing the integrase to an integrase inhibiting amount of one or more anti-integrase compounds, or pharmaceutically acceptable salts, of

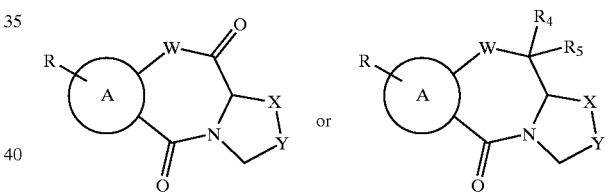

wherein A is thiazole, benzene, naphthalene, pyridine, pyrimidine, pyrazine, or quinoline; R is one or more of H, halogen, lower alkyl, lower alkoxy, $NO_2$, lower ester or carboxylic acid; X—Y is $CH_2$—S, S—$CH_2$, $CH_2$—O, $CH_2$—S(O), S(O)—$CH_2$, $CH_2$—$CH_2$, $CH_2$—$CH_2$—$CH_2$, or $CH_2$—$CH_2$—$CH_2$—$CH_2$; $R_4$ is H or hydroxy; $R_5$ is H, phenyl, or alkylamine; and W is S or O or wherein the compound is

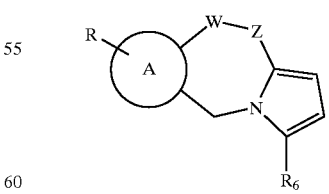

wherein A is thiazole, benzene, naphthalene, pyridine, pyrimidine, pyrazine, or quinoline; and R is one or more of H, halogen, lower alkyl, lower ester or carboxylic acid; $R_6$ is H, substituted or unsubstituted alkyl or amine; W is S or O; and Z is S, O, $CH_2$, $CH_2CH_2$, or C=O.

In yet other embodiments, the compound is selected from the group of

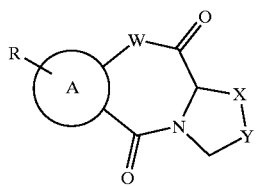 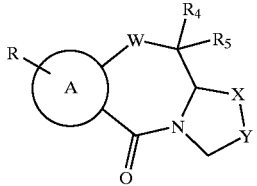

wherein X—Y is CH$_2$—S, S—CH$_2$, CH$_2$—O, or CH$_2$—CH$_2$, and W is S. In particular compounds, A is benzene, naphthalene, pyridine, pyrimidine, pyrazine, or quinoline, and in particular benzene or naphthalene. In other particular examples, R is H, halogen, lower alkoxy, or NO$_2$.

In another aspect of the invention, the compound is one or more of:

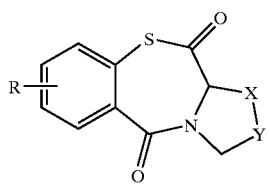

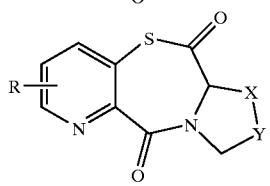

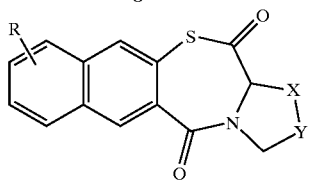

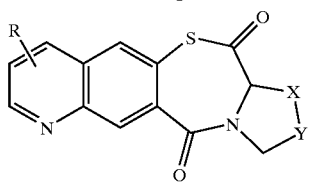

In yet other embodiments, the compound is one or more of:

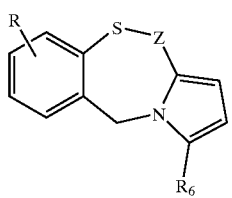 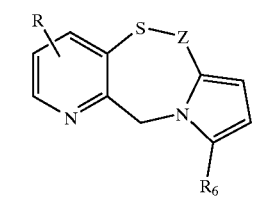

In more specific embodiments, the compound is one or more of:

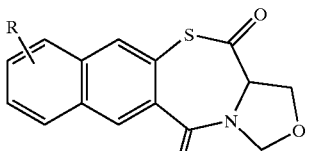

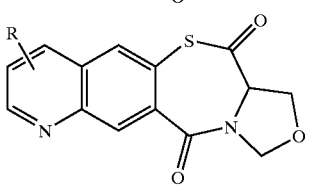

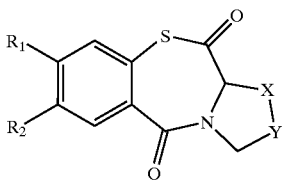

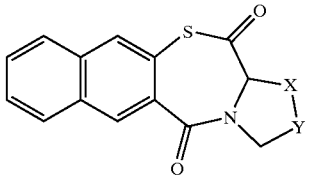

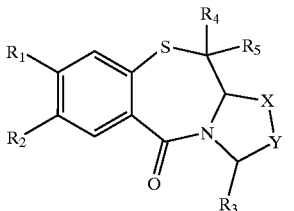

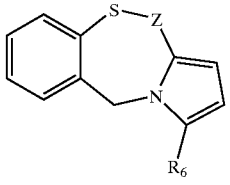

wherein X—Y is S—CH$_2$, CH$_2$—S, CH$_2$—O, CH$_2$—CH$_2$, S(O)—CH$_2$, or CH$_2$—S(O); R$_1$ and R$_2$ are independently selected from the group consisting of H, NO$_2$, halogen, lower alkyl or lower alkoxy; R$_3$ is H or phenyl; R$_4$ is H or hydroxy; R$_5$ is H, phenyl or alkylamine; and R$_6$ is H, phenyl or alkylamine.

In particular embodiments, the alkylamine is —N(CH$_2$CH$_2$)$_2$NCH$_3$, —CH$_2$NCH$_2$CH$_3$, or —CH$_2$N(CH$_2$CH$_2$)$_2$NCH$_3$.

A particular group of compounds with superior anti-integrase activity is

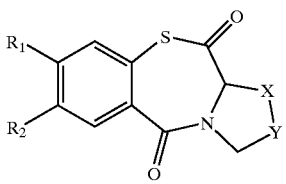

-continued

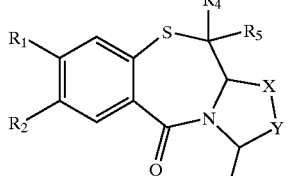

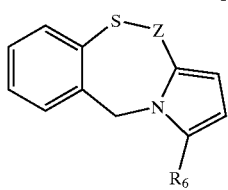 or

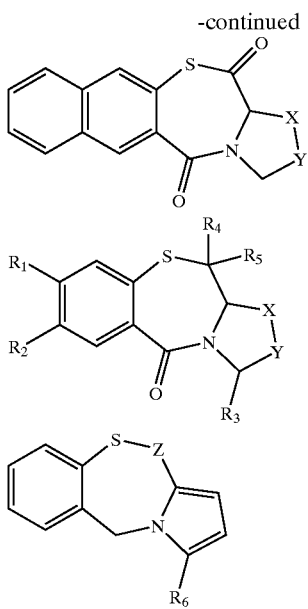

wherein X—Y is S—CH$_2$, CH$_2$—S, or CH$_2$—S(O); and R$_1$ and R$_2$ are independently selected from the group consisting of H, NO$_2$, halogen, lower alkyl and lower alkoxy; R$_3$ is H; and R$_4$, R$_5$, and R$_6$ are H. An example of such a compound is

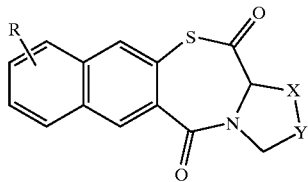

wherein X—Y is S—CH$_2$ or CH$_2$—S, and for example where R is H and X—Y is S—CH$_2$.

In other embodiments, in which the compounds have particularly good antiviral activity, R$_1$ is H, NO$_2$, or lower alkoxy; R$_2$ is H, Cl, Br, lower alkyl, or lower alkoxy; R$_3$ and R$_4$ are H; R$_5$ is N(CH$_2$CH$_2$)$_2$NCH$_3$; and X—Y is CH$_2$—S, S—CH$_2$, or CH$_2$—CH$_2$, and particularly:

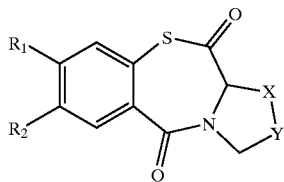

wherein R$_1$ is H, NO$_2$, or methoxy; R$_2$ is H, halogen or methoxy; and X—Y is CH$_2$—S or S—CH$_2$, especially S—CH$_2$.

The invention also includes methods of administering any of the above compounds in a therapeutically effective amount to a subject, for example to treat or prevent HIV infection in the subject. In particular examples, the compound which is administered is selected from the group of

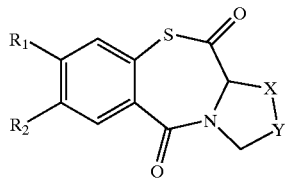

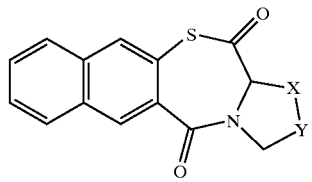

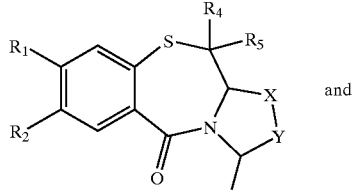 and

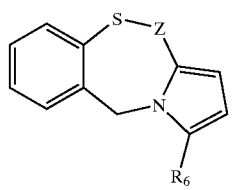

wherein X—Y is S—CH$_2$, CH$_2$—S, CH$_2$CH$_2$ or S(O)CH$_2$; R$_1$ is H, NO$_2$, or lower alkoxy; R$_2$ is H, Cl, Br, lower alkyl, or lower alkoxy; R$_3$ and R$_4$ are H; R$_5$ is N(CH$_2$CH$_2$)$_2$NCH$_3$; and R$_6$, is H, and in particular:

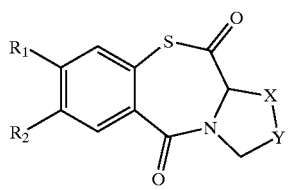

wherein R$_1$ and R$_2$ are H, and X—Y is S—CH$_2$; or R$_1$ is H, R$_2$ is Cl or Br or methyl, and X—Y is S—CH$_2$; or R$_1$ is NO$_2$, R$_2$ is H, and X—Y is CH$_2$—S; or R$_1$ and R$_2$ are methoxy, and X—Y is CH$_2$—S; or R$_1$ is H, R$_2$ is methyl, and X—Y is S(O)—CH$_2$; or

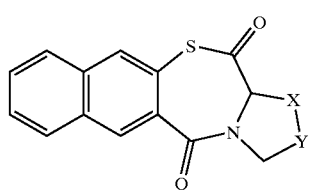

wherein X—Y is S—CH$_2$ or CH$_2$—S; or

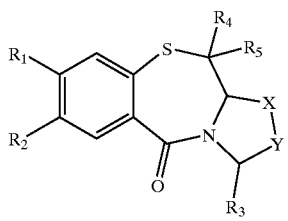

wherein X—Y is CH$_2$—CH$_2$; R$_1$, R$_2$, R$_3$ and R$_4$ are H; and R$_5$ is N(CH$_2$CH$_2$)$_2$NCH$_3$; or

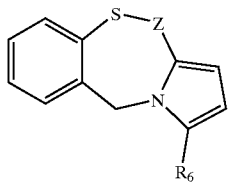

wherein R$_6$ is H and Z is C=O.

In other embodiments, R is one or more of halogen or NO$_2$; X—Y is CH$_2$—S, S—CH$_2$, CH$_2$—O, CH$_2$—S(O), S(O)—CH$_2$, CH$_2$—CH$_2$, CH$_2$—CH$_2$—CH$_2$, or CH$_2$—CH$_2$—CH$_2$—CH$_2$; R$_4$ is H or hydroxy, particularly hydroxy; R$_5$ is H, phenyl, or alkylamine; and W is S or O; R$_6$ is H, substituted or unsubstituted alkyl or amine; Z is S, O, CH$_2$, CH$_2$CH$_2$, or C=O, particularly C=O.

In particular embodiments, the method includes administration of:

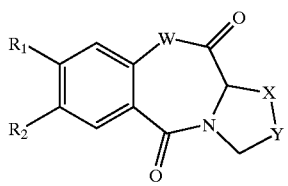

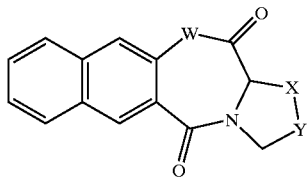

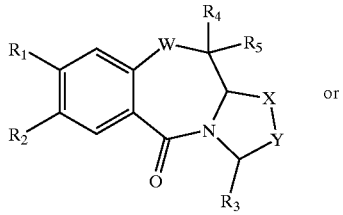

or

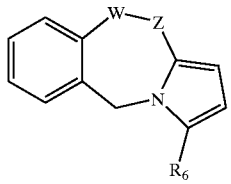

wherein X—Y is S—CH$_2$, CH$_2$—S, S(O)—CH$_2$, CH$_2$—S(O), or CH$_2$CH$_2$; W is S or O; R$_1$ is H or NO$_2$; R$_2$ is H, halogen, lower alkyl or lower alkoxy; R$_3$ is H; R$_4$ is hydroxy or H; R$_5$ is phenyl or N(CH$_2$CH$_2$)$_2$NCH$_3$; and R$_6$ is CH$_2$N(CH$_2$CH$_2$)$_2$NCH$_3$, provided that R$_1$ and R$_2$ are not both H or not both lower alkoxy (such as methoxy).

For example, the administered compound can be

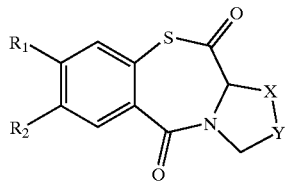

wherein R$_1$ is H or NO$_2$; R$_2$ is H, halogen, lower alkyl or lower alkoxy; provided that R$_1$ and R$_2$ are not both H or lower alkoxy; or wherein R$_1$ is H, R$_2$ is Cl, X—Y is S—CH$_2$; or R$_1$ is H, R$_2$ is Br, X—Y is S—CH$_2$; or R$_1$ is H, R$_2$ is CH$_3$, X—Y is S—CH$_2$; or R$_1$ is H, R$_2$ is H, X—Y is CH$_2$—S; or R$_1$ is H, R$_2$ is Cl, X—Y is CH$_2$—S; or R$_1$ is H, R$_2$ is Br, X—Y is CH$_2$—S; or R$_1$ is H, R$_2$ is CH$_3$, X—Y is CH$_2$—S; or R$_1$ is NO$_2$, R$_2$ is H, X—Y is CH$_2$—S; or R$_1$ is H, R$_2$ is OCH$_3$, X—Y is CH$_2$—S; or R$_1$ is H, R$_2$ is H, X—Y is CH$_2$—O; or R$_1$ is H, R$_2$ is CH$_3$, X—Y is S(O)—CH$_2$; or R$_1$ is H, R$_2$ is H, X—Y is CH$_2$—S(O); or R$_1$ is H, R$_2$ is Cl, X—Y is CH$_2$—S(O); or R$_1$ is H, R$_2$ is OCH$_3$, X—Y is CH$_2$—S(O).

In particular, X—Y may be S—CH$_2$. Alternatively, R$_1$, R$_2$ and R$_3$ are H, R$_4$ is OH or H, R$_5$ is Ph or N(CH$_2$CH$_2$)$_2$CH$_3$, and X—Y is CH$_2$—CH$_2$.

Alternatively, the compound can be:

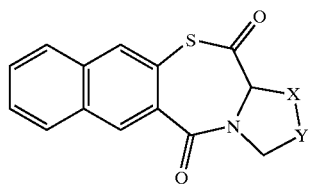

wherein X—Y is S—CH$_2$ or CH$_2$—S.

The compound can also be:

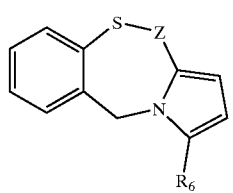

wherein R$_6$ is CH$_2$N(CH$_2$CH$_2$)$_2$NCH$_3$.

The invention also includes a pharmaceutical composition that includes the compound, or a pharmaceutically acceptable salt thereof, and a pharmaceutically acceptable carrier. Also included are methods of screening for an anti-HIV integrase drug, by providing an assay of HIV integrase inhibition, and using the assay to screen for drugs that are analogs or derivatives of any of the compounds, and which inhibit HIV integrase. In particular embodiments, the assay detects a thiazepine compound that inhibits human immunodeficiency virus type-1 integrase (HIV-1 IN), and particularly such a compound that has no detectable effect on reverse transcriptase, protease, and virus attachment. In very particular examples, the compounds that are screened are thiazolothiazepines.

DETAILED DESCRIPTION OF PARTICULAR EXAMPLES

Definitions

Figure 1:
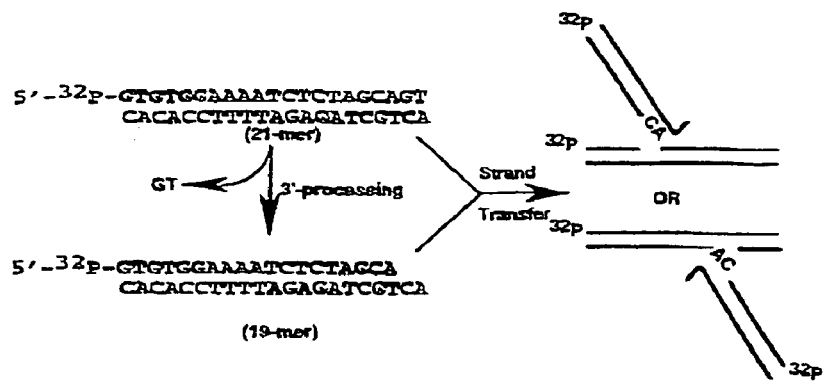
FIG. 1 is a schematic diagram illustrating an assay for integrase mediated integration of HIV DNA into the host cell genome. A 21-mer blunt-end oligonucleotide corresponding to the U5 end of the HIV-1 LTR, 5' end-labeled with $^{32}P$, is reacted with purified integrase. The enzyme causes nucleolytic cleavage of two bases from the 3'-end (3' processing), resulting in a 19-mer oligonucleotide. Subsequently, 3' ends are covalently joined to another identical oligonucleotide that serves as the target DNA (strand transfer reaction).

A "benzothiazepine" refers to a benzodiazepine in which one of the ring nitrogens has been replaced with a sulfur, for example:

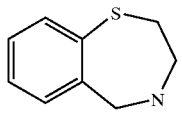

while a "thiazolothiazepine" refers to a benzothiazepine having a thiazolo ring, for example:

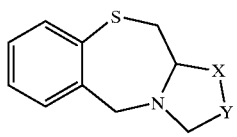

in which X—Y is $CH_2$—S or S—$CH_2$.

The term "alkyl" refers to a cyclic, branched, or straight chain alkyl group containing only carbon and hydrogen, and unless otherwise mentioned contains one to twelve carbon atoms. This term is further exemplified by groups such as methyl, ethyl, n-propyl, isobutyl, t-butyl, pentyl, pivalyl, heptyl, adamantyl, and cyclopentyl. Alkyl groups can either be unsubstituted or substituted with one or more substituents, e.g. halogen, alkyl, alkoxy, alkylthio, trifluoromethyl, acyloxy, hydroxy, mercapto, carboxy, aryloxy, aryloxy, aryl, arylalkyl, heteroaryl, amino, alkylamino, dialkylamino, morpholino, piperidino, pyrrolidin-1-yl, piperazin-1-yl, or other functionality.

The term "lower alkyl" refers to a cyclic, branched or straight chain monovalent alkyl radical of one to five carbon atoms. This term is further exemplified by such radicals as methyl, ethyl, n-propyl, i-propyl, n-butyl, t-butyl, i-butyl (or 2-methylpropyl), cyclopropylmethyl, i-amyl, and n-amyl. Lower alkyl groups can also be unsubstituted or substituted, where a specific example of a substituted alkyl is 1,1-dimethyl propyl.

"Carboxyl" refers to the radical —COOH, and substituted carboxyl refers to —COR where R is alkyl, lower alkyl or a carboxylic acid or ester.

The term "aryl" refers to a monovalent unsaturated aromatic carbocyclic group having a single ring (e.g. phenyl) or multiple condensed rings (e.g. naphthyl or anthryl), which can optionally be unsubstituted or substituted with, e.g., halogen, alkyl, alkoxy, mercapto (—SH), alkylthio, trifluoromethyl, acyloxy, hydroxy, mercapto, carboxy, aryloxy, aryl, arylalkyl, heteroaryl, amino, alkylamino, dialkylamino, morpholino, piperidino, pyrrolidin-1-yl, piperazin-1-yl, or other functionality.

The term "alkoxy" refers to a substituted or unsubstituted alkoxy, where an alkoxy has the structure —O—R, where R is substituted or unsubstituted alkyl. In an unsubstituted alkoxy, the R is an unsubstituted alkyl. The term "substituted alkoxy" refers to a group having the structure —O—R, where R is alkyl which is substituted with a non-interfering substituent. "Lower alkoxy" refers to any alkoxy in which R is a lower alkyl.

The term "heterocycle" refers to a monovalent saturated, unsaturated, or aromatic carbocyclic group having a single ring (e.g. benzyl, morpholino, pyridyl or furyl) or multiple condensed rings (e.g. naphthyl, quinolinyl, indolizinyl or benzo[b]thienyl) and having at least one heteroatom, defined as N, O, P, or S, within the ring, which can optionally be unsubstituted or substituted with, e.g. halogen, alkyl, alkoxy, alkylthio, trifluoromethyl, acyloxy, hydroxy, mercapto, carboxy, aryloxy, aryl, arylalkyl, heteroaryl, amino, alkylamino, dialkylamino, morpholino, piperidino, pyrrolidin-1-yl, piperazin-1-yl, or other functionality.

The term "halogen" refers to fluoro, bromo, chloro and iodo substituents.

The term "amino" refers to a chemical functionality —$NR_1R_2$ where $R_1$ and $R_2$ are independently hydrogen, alkyl, or aryl.

A "pharmaceutical agent" or "drug" refers to a chemical compound or composition capable of inducing a desired therapeutic or prophylactic effect when properly administered to a subject.

The pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof.

All chemical compounds include both the (+) and (−) stereoisomers, as well as either the (+) or (−) stereoisomer.

An analog is a molecule, that differs in chemical structure from a parent compound, for example a homolog (differing by an increment in the chemical structure, such as a difference in the length of an alkyl chain), a molecular fragment, a structure that differs by one or more functional groups, or a change in ionization. Structural analogs are often found using quantitative structure activity relationships (QSAR), with techniques such as those disclosed in *Remington: The Science and Practice of Pharmacology*, 19$^{th}$ Edition (1995), chapter 28. A derivative is a biologically active molecule derived from the base structure. A mimetic is a biomolecule that mimics the activity of another biologically active molecule. Biologically active molecules can include both chemical structures and peptides of protein entities that mimic the biological activities of the mercaptosalicylhydrazides of the present invention.

Other chemistry terms herein are used according to conventional usage in the art, as exemplified by *The McGraw-Hill Dictionary of Chemical Terms* (1985) and *The Condensed Chemical Dictionary* (1981).

A "mammal" includes both human and non-human mammals. Similarly, the term "subject" includes both human and veterinary subjects.

An animal is a living multicellular vertebrate organism, a category which includes, for example, mammals and birds.

"HIV disease" refers to a well recognized constellation of signs and symptoms (including the development of opportunistic infections) in persons who are infected by an HIV virus, as determined by antibody or western blot studies. Laboratory findings associated with this disease are a progressive decline in T-helper cells.

Materials and Methods

Where necessary, solvents were dried and purified according to the recommended procedures. All reactions were carried out under an argon atmosphere. Progress of the reaction was monitored by TLC on silica gel plates (Riedel-de-Haen, Art. 37341). Organic solutions were dried over $MgSO_4$, evaporation refers to removal of solvent on a rotary evaporator under reduced pressure. Melting points were determined using an Electrothermal 8103 apparatus and are uncorrected. Optical rotations were measured on an Optical Activity AA-5 polarimeter. IR spectra were recorded as thin films on Perkin-Elmer 398 and FT 1600 spectrophotometers. $^1$H NMR spectra were recorded on a Bruker 200 MHz spectrometer with TMS as internal standard; the values of chemical shifts (δ) are given in ppm and coupling constants (J) in Hz. Mass spectral data were determined by direct insertion at 70 eV with a VG70 spectrometer. Merck silica gel (Kieselgel 60/230,400 mesh) was used for flash chromatography columns. Dowex 50×2 200 resin (Aldrich) was used for ion-exchange chromatography. Elemental analyses were performed on a Perkin-Elmer 240C elemental analyzer, and the results are within ±0.4% of the theoretical values. Yields refer to purified products and are not optimized.

Compound Reference Numbers

Compounds are identified throughout this detailed description using reference numerals in bold, which correspond to the identification of the compounds in Table 1, and in the following examples.

EXAMPLE 1

Synthesis of Thiazolothiazepines

The synthesis of compounds 1, 5, 11, 13–14, 21–25 and 28–30 (see Table 1 for an identification of these compounds) has been accomplished according to general or similar procedures reported elsewhere.[15–20] Compounds 2–4, 6–10, 12 and 19–20 (Table 1) have been prepared following the general method outlined in Scheme 1:

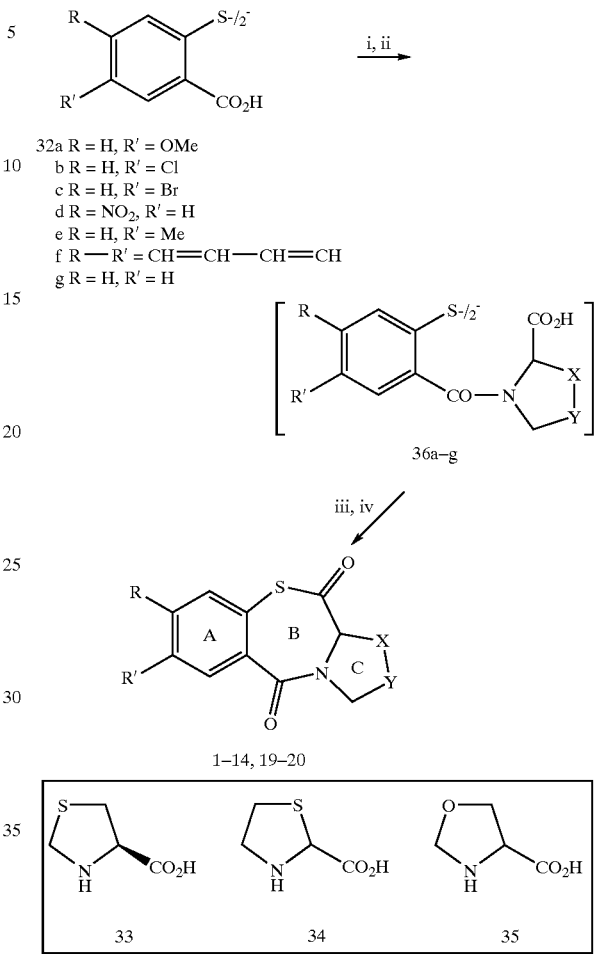

Schotten-Baumann reaction between the (un)substituted 2,2'-dithiobis(benzoic acid chloride) or 3,3'-dithiobis(2,2'-naphtoic acid chloride), in turn obtained from corresponding acids 32a–g[21–25] and thionyl chloride, and L-thiaproline (Aldrich) (33) or thiazolidine-2-carboxylic acid (34) or 1,3-oxazolidine-4-carboxylic acid (35) (Chart 1) gave disulfides 36. $NaBH_4$ reduction of the crude disulfides gave the corresponding thiophenols in very good yield. Disulfides 36 and subsequent thiophenols were obtained as amorphous solids by ion-exchange chromatography and were then used without a thorough characterization. The eventual cyclization reaction was carried out using N,N'-carbonyldiimidazole (CDI) in dry THF leading to optically inactive tricyclics 2–4, 6–10, 12 and 19–20 because of racemization at C-11a (C-13a in the case of compounds 19 and 20).

Controlled 3-chloroperbenzoic acid (MCPBA) oxidation of the tricyclic sulfides 4–6 and 10 gave sulfoxides 15–18 (Scheme 2) which were tentatively assigned a cis configuration on the basis of $^1$H NMR experiments and Dreiding stereomodels inspection. This would reflect a preferred approach of the electrophile from the less hindered face of the tricyclic ring, namely the one taken up by the C-.11a proton. Example 4 provides more details about synthesis of the sulfoxides 15–18.

Scheme 2

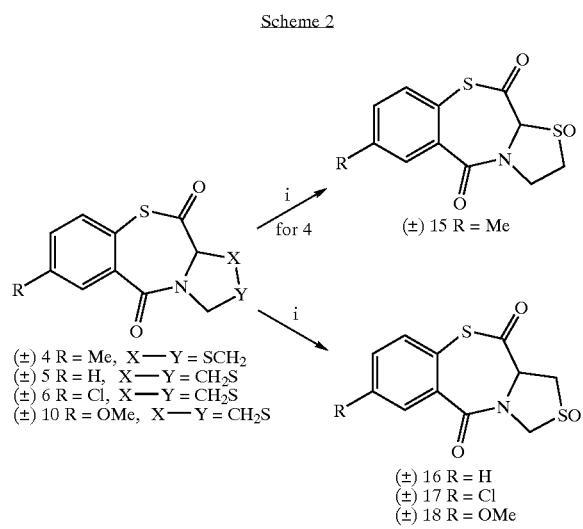

(±) 4 R = Me, X—Y = SCH₂
(±) 5 R = H, X—Y = CH₂S
(±) 6 R = Cl, X—Y = CH₂S
(±) 10 R = OMe, X—Y = CH₂S (±) 15 R = Me (±) 16 R = H
(±) 17 R = Cl
(±) 18 R = OMe

Reagents: (i) MCPBA/CH₂Cl₂/0° C.

Compound 26 was obtained as a racemic mixture by reaction of previously described (±)-1,2,3,11a-tetrahydro-5H,11H-pyrrolo[2,1-c][1,4]benzothiazepine-5,11-dione (37) with phenyl magnesium bromide in dry conditions (Scheme 3).

Scheme 3

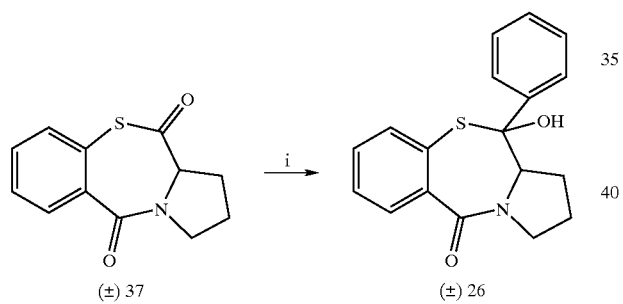

(±) 37       (±) 26

Reagents: (i) PhMgBr/Et₂O.

The basic side chain of compound 27 was installed by means of reaction of 1-methylpiperazine on optically active chloro derivative 38 (Scheme 4).

Scheme 4

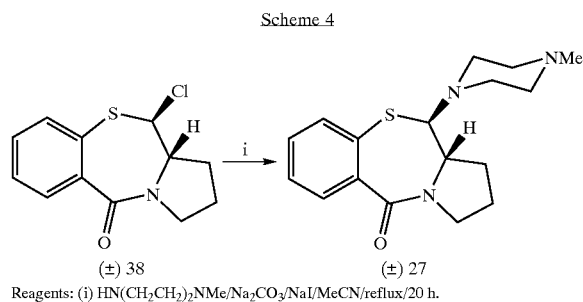

(±) 38       (±) 27

Reagents: (i) HN(CH₂CH₂)₂NMe/Na₂CO₃/NaI/MeCN/reflux/20 h.

In the reaction conditions used, a racemic mixture of cis 27 was the sole product obtained. Finally, the synthesis of compound 31 was carried out by Mannich reaction on the α-pyrrole position of (±)-11-phenyl-5H,11H-pyrrolo[2,1-c][1,4]benzothiazepine (39) by means of paraformaldehyde and 1-methylpiperazine dihydrochloride in methanol (Scheme 5).

Scheme 5

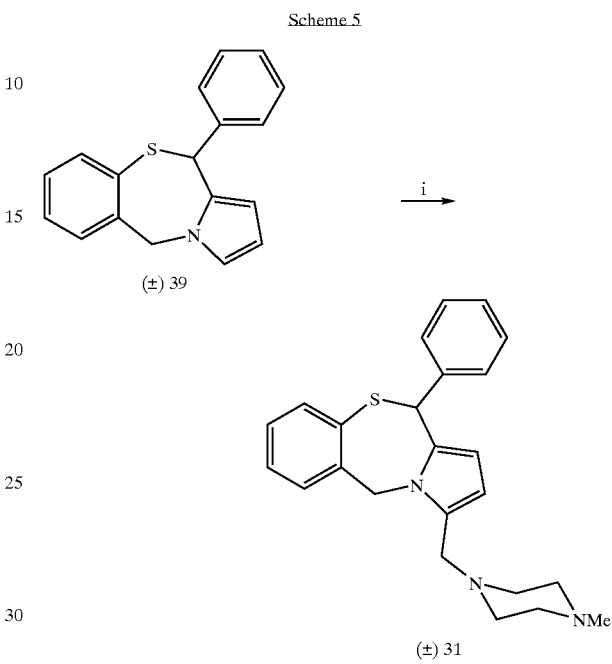

(±) 39

(±) 31

Reagents: (i) CH₂O/HN(CH₂CH₂)₂NMe.₂HCl/MeOH.reflux 48 h.

EXAMPLE 2

Procedure for the Preparation of Thiazepine 10

This example illustrates the preparation of (±)-1,11a-dihydro-7-methoxy-3H,5H, 11H-thiazolo[4,3-c][1,4]benzothiazepine-5,11-dione (10). A mixture of 2,2'-dithiobis(5-methoxybenzoic acid) (5.5 g, 15 mmol) (32a) and thionyl chloride (40 mL) was refluxed for 1.5 hours. After cooling, the excess of thionyl chloride was removed under vacuum using dry benzene (2×5 mL). The resulting solid was dissolved in dry THF (40 mL) and the solution was added dropwise to a mixture of L-thiaproline (33) (4.0 g, 30.0 mmol) and sodium carbonate (3.2 g, 15.0 mmol) in water (50 mL). Additional sodium carbonate was added from time to time to maintain a weakly alkaline pH. The mixture was stirred overnight, then concentrated and made acidic (pH 34) by adding concentrated HCl. The gummy solid was extracted into ethyl acetate and the resulting solution was washed with water, dried, and evaporated to give foam. Ion-exchange column chromatography using methanol as the eluent gave almost pure disulfide 36a as an amorphous solid.

The solid (8.95 g, 15 mmol) was dissolved in 85% ethanol (100 mL) containing NaOH (1.2 g, 30 mmol), and to this was added a solution of NaBH₄ (1.14 g, 30 mmol) in ethanol (50 mL). The mixture was gently refluxed for 0.5 hour, then concentrated and diluted with chilled-water. The cold solution was left for 15 minutes before being filtered and made acidic (pH 3–4) by concentrated HCl. The gummy solid was treated exactly as described before for purification of compound 36a and then thoroughly dried under vacuum before being subjected to the successive reaction without further manipulation. Crude thiophenol derivative (6.0 g, 20.0 mmol) was dissolved into dry THF (80 mL) and N,N'-carbonyldiimidazole (3.24 g, 20.0 mmol) was added in portions. The solution was stirred for 24 hours, and then for 2 hours under reflux. The solvent was evaporated and the residue was partitioned between CHCl₃ and 0.5 N HCl. The organic solution was separated and washed with NaHCO₃ saturated solution and water.

After drying and evaporation of the solvent, a pasty residue was obtained and purified by flash chromatography (8% methanol in EtOAc) to give 4.2 g (74% yield from the thiophenol precursor) of 10 as a white powder. Analysis revealed mp 145–147° C. (benzene); IR (KBr) 1700, 1640 cm$^{-1}$; $^1$H NMR (CDCl₃) δ7.46 (d, 1H, J=2.8 Hz), 7.35 (m, 1H), 7.04 (dd, 1H, J=8.1, 2.8 Hz), 4.79 (AB q, 2H, J=10.2 Hz), 4.60 (dd, 1H, J=6.6, 1.5 Hz), 3.87 (s, 3H), 3.64 (dd, 1 H, J=12.7, 1.5 Hz), 3.15 (dd, 1H, J=12.7, 6.6 Hz). Anal. ($C_{12}H_{11}NO_3S_2$) C, H, N.

EXAMPLE 3

Synthesis and Analytical Results for Compounds 2–4, 6–9, 12, 19–20, 26–27, and 31

(±)-7-Chloro-2,3-dihydro-5H-thiazolo[2,3-c][1,4]benzothiazepine-5,11 (11aH)-dione (2). Starting from 2,2'-dithiobis(5-chlorobenzoic acid) (32b) (5.6 g, 15 mmol), the title compound 2 was obtained (3.6 g, 63% yield from the thiophenol precursor) adopting the same procedure as for 10, but using thiazolidine-2-carboxylic acid 34 instead of L-thiaproline 33: mp 231–232° C. (benzene); IR (KBr) 1695, 1640 cm$^{-1}$; $^1$H NMR (CDCl₃) δ7.98 (d, 1H, J=2.4 Hz), 7.52–7.38 (m, 2H), 5.35 (s, 1H), 4.03 (m, 2H), 3.16 (m, 2H). Anal. ($C_{11}H_8ClNO_2S_2$)C, H, N.

(±)-7-Bromo-2,3-dihydro-5H-thiazolo[2,3-c][1,4]benzothiazepine-5,11 (11aH)-dione (3). Starting from 2,2'-dithiobis(5-bromobenzoic acid) (32c)$^{22}$ (7.0 g, 15 mmol), the compound 3 was obtained (4.0 g, 70% yield from the thiophenol precursor) adopting the same procedure as for 10, but using thiazolidine-2-carboxylic acid 34 instead of L-thiaproline 33: mp 219–220° C. (benzene); IR (KBr) 1695, 1640 cm$^{-1}$; $^1$H NMR (CDCl₃) δ8.11 (d, 1H, J=2.2 Hz), 7.62 (dd, 1H, J=8.3, 2.2 Hz), 7.32 (dd, 1H, J=8.3, 2.2 Hz), 5.33 (s, 1H), 4.00 (m, 2H), 3.18 (m, 2H). Anal. ($C_{11}H_8BrNO_2S_2$)C, H, N.

(±)-2,3-Dihydro-7-methyl-5H-thiazolo[2,3-c][1,4]benzothiazepine-5,11 (11aH)-dione (4). Starting from 2,2'-dithiobis(5-methylbenzoic acid) (32e) (5.0 g, 15.0 mmol), the compound 4 was obtained (5.6 g, 76% yield from the thiophenol precursor) adopting the same procedure as for 10, but using thiazolidine-2-carboxylic acid 34 instead of L-thiaproline 33: mp 197–199° C. (benzene-petroleum ether); IR (KBr) 1690, 1645 cm$^{-1}$; $^1$H NMR (CDCl₃) δ7.79 (s, 1H,), 7.29 (m, 2H), 5.36 (s, 1H), 4.02 (m, 2H), 3.12 (m, 2H), 2.42 (s, 3H). Anal. ($C_{12}H_{11}NO_2S_2$)C, H, N.

(±)-7-Chloro-1,11a-dihydro-3H,5H,11H-thiazolo[4,3-c][1,4]benzothiazepine-5,11-dione (6). Starting from 2,2'-dithiobis(5-chlorobenzoic acid) (32b) (5.6 g, 15 mmol), the compound 7 was obtained (4.0 g, 70% yield from the thiophenol precursor) using the same procedure as for 10: mp 204–205 ° C. (benzene). IR (KBr) 1705, 1640 cm$^{-1}$; $^1$H NMR (CDCl₃) δ7.96 (d, 1H, J=2.0), 7.51–7.38 (m, 2H), 4.80 (AB q, 2H, J=10.7 Hz), 4.57 (dd, 1H, J= 6.9, 1.7 Hz), 3.67 (dd, 1H, J=11.9, 1.7 Hz), 3.19 (dd, 1H, J=11.9, 6.9 Hz). Anal. ($C_{11}H_8ClNO_2S_2$) C, H, N.

(±)-7-Bromo-1,11a-dihydro-3H,5H,11H-thiazolo[4,3-c][1,4]benzothiazepine-5,11-dione (7). Starting from 2,2'-dithiobis(5-bromobenzoic acid) (32c) (7.0 g, 15 mmol), the compound 8 was obtained (4.1 g, 63% yield from the thiophenol precursor) using the same procedure as for 10: mp 213–214° C. (benzene). IR (KBr) 1700, 1635 cm$^{-1}$; $^1$H NMR (CDCl₃) δ8.10 (t, 1H, J=1.0 Hz), 7.63 (dd, 1H, J=8.0, 1.0), 7.34 (d, 1H, J=8.0), 4.81 (AB q, 2H, J=10.6 Hz), 4.55 (dd, 1H, J=6.0, 1.9 Hz), 3.67 (dd, 1H, J=11.8, 1.9 Hz), 3.18 (dd, 1H, J=11.8, 6.0 Hz). Anal. ($C_{11}H_8BrNO_2S_2$)C, H, N.

(±)-1,11a-Dihydro-7-methyl-3H,5H,11H-thiazolo[4,3-c][1,4]benzothiazepine-5,11-dione (8). Starting from 2,2'-dithiobis(5-methylbenzoic acid) (32e) (5.0 g, 15.0 mmol), the compound 8 (6.1 g, 82% yield from the thiophenol precursor) was obtained as a thick oil, using the same procedure as for 10: IR (KBr) 1695, 1640 cm$^{-1}$; $^1$H NMR (CDCl₃) δ7.74 (s, 1H,), 7.30 (m, 2 H), 4.77 (AB q, 2H, J=10.2 Hz), 4.60 (dd, 1H, J=6.8, 1.7 Hz), 3.62 (dd, 1 H, J=12.1, 1.7 Hz), 3.23 (dd, 1H, J=12.1, 6.8 Hz), 2.40 (s, 3H). Anal. ($C_{12}H_{11}NO_2S_2$)C, H, N.

(±)-1,11a-Dihydro-8-nitro-3H,5H,11H-thiazolo[4,3-c][1,4]benzothiazepine-5,11-dione (9). Starting from 2,2'-dithiobis(4-nitrobenzoic acid) (32d) (5.9 g, 15 mmol), the compound 9 was obtained (2.0 g, 34% from the thiophenol precursor) using the same procedure as for 10: mp 231–232° C. (benzene-petroleum ether); IR (KBr) 1715, 1645 cm$^{-1}$; $^1$H NMR (CDCl₃) δ8.35 (s, 1H,), 8.32 (dd, 1H, J=8.1, 2.0 Hz), 8.16 (d, 1H, J=8.1 Hz), 4.84 (AB q, 2H, J=10.5 Hz), 4.54 (dd, 1H, J=6.4, 1.5 Hz), 3.70 (dd, 1H, J=11.9, 1.5 Hz), 3.23 (dd, 1H, J=11.9, 6.4 Hz). Anal. ($C_{11}H_8N_2O_4S_2$)C, H, N.

(±)-1,11a-Dihydro-3H,5H,11H-oxazolo[4,3-c][1,4]benzothiazepine-5,11-dione (12). Starting from commercial 2,2'-dithiodibenzoic acid (32g) (4.6 g, 15.0 mmol), the compound 12 was obtained as a thick oil (3.0 g, 42% yield from the thiophenol precursor) adopting the same procedure as for 10, but using freshly prepared 1,3-oxazolidine-4-carboxylic acid 32$^{27}$ (3.5 g, 30.0 mmol) instead of L-thiaproline 33: IR (KBr) 1690, 1635 cm$^{-1}$; $^1$H NMR (CDCl₃) δ7.50 (m, 1H,), 7.22 (m, 3H), 5.22 (AB q, 2H, J=5.3 Hz), 4.81 (dd, 1H, J=8.8, 1.7 Hz), 4.25 (dd, 1H, J=5.9, 1.6 Hz), 3.98 (dd, 1H, J=8.9, 5.9 Hz). MS m/z 235 (M⁺), 207, 177, 150, 136 (100), 108. Anal. ($C_{11}H_9NO_3S$)C, H, N.

(±)-2,3-Dihydro-5H-naphto[2,3-f]thiazolo[2,3-c][1,4]thiazepine-5,13(13aH)-dione (19). Starting from 3,3'-dithiobis(2,2'-naphtoic acid) (32f) (1.22 g, 1.5 mmol), the compound 19 (0.27 g, 30% yield from the thiophenol precursor) was obtained, adopting the same procedure as for 10, but using thiazolidine-2-carboxylic acid 34 instead of L-thiaproline 33 and carrying out the NaBH₄ reduction of the disulfide overnight at room temperature: mp 196–198° C.; IR (KBr) 1700, 1630 cm$^{-1}$; $^1$H NMR (CDCl₃) δ8.52 (s, 1H), 7.99 (s, 1H), 7.93 (m, 1H), 7.84 (m, 1H,), 7.63 (m, 2H), 5.40 (s, 1H), 4.11 (m, 2H), 3.16 (m, 2H). MS m/z 301 (M⁺), 273 (100), 186, 158, 142, 114. Anal. ($C_{15}H_{11}NO_2S_2$)C, H, N.

(±)-1,13a-Dihydro-3H,5H,11H-naphto[2,3-f]thiazolo[4,3-c][1,4]thiazepine-5,13-dione (20). Starting from 3,3'-dithiobis(2,2'-naphtoic acid) (32f) (1.22 g, 1.5 mmol), the compound 20 (0.34 g, 38% yield from the thiophenol precursor) was obtained, using the same procedure as for 10, but carrying out the NaBH₄ reduction of the disulfide overnight at room temperature: mp 200–203° C.; IR (KBr) 1695, 1630 cm$^{-1}$; $^1$H NMR (CDCl₃) δ8.51 (s, 1H), 7.98 (s, 1H), 7.94 (m, 1H), 7.84 (m, 1H,), 7.58 (m, 2H), 4.85 (AB q, 2H, J=10.6 Hz), 4.66 (dd, 1H, J=6.9, 1.6 Hz), 3.65 (dd, 1H, J=11.8, 1.5 Hz), 3.14 (dd, 1 H, J=12.1, 6.7 Hz). MS m/z 301 (M⁺), 273 (100), 186, 158, 142, 114. Anal. ($C_{15}H_{11}NO_2S_2$) C, H, N.

(±)-2,3,11,11a-Tetrahydro-11-hydroxy-11-phenyl-1H, 5H-pyrrolo [2,1-c][1,4]benzothiazepin-5-one (26). A solution of compound 37$^{16}$ (0.88 g, 3.8 mmol) in dry THF (10 mL) was dropwise added to a solution of PhMgBr in ethyl ether [obtained from 1.23 g of PhBr, 0.185 g of Mg turnings and 8 mL of Et₂O]. The mixture was refluxed for 30 min, then cooled to rt and quenched by the addition of NH₄Cl saturated solution. Chloroform extraction and evaporation gave a residue which was purified by column chromatography to give the title compound 26 (0.7 g, 59% yield) along with some other unidentified by-products. The title compound was obtained as colorless crystals by crystallization: mp 137–141° C. (ethanol); IR (KBr) 3210 broad, 1620 cm$^{-1}$; $^1$H NMR (CDCl$_3$) δ8.02 (m, 1H), 7.85 (m, 1H), 7.60–7.10 (m, 7H), 3.87 (m, 1H), 3.55 (m, 2H), 3.08 (br s, 1H), 1.95 (m, 4H). Anal. (C$_{18}$H$_{17}$NO$_2$S)C, H, N.

(±)-cis-2,3,11,11a-Tetrahydro-11-(4-methylpiperazin-1-yl)-1H,5H-pyrrolo[2,1-c][1,4]benzothiazepin-5-one (27). A mixture of (+)-11-chloro-2,3,11,11a-tetrahydro-1H,5H,-pyrrolo[2,1-c][1,4]benzothiazepin-5-one (38)[15] (0.6 g, 2.4 mmol), freshly distilled 1-methylpiperazine (0.34 mL, 3.1 mmol), Na$_2$CO$_3$(1.06 g, 10.0 mmol), NaI (0.36 g, 2.4 mmol) in dry CH$_3$CN (30 mL) was gently refluxed for 20 hours. The solvent was evaporated and the residue was partitioned between CH$_2$Cl$_2$ and water. The organic phase was successively washed with a 2% solution of Na$_2$S$_2$O$_3$, water and brine. The residue obtained after evaporation was chromatographed on silica gel eluting with 5% methanol in CH$_2$Cl$_2$. The title compound 27 was obtained as a white solid (0.55 g, 73% yield): mp 188–190° C. (2-propanol-isopropyl ether); IR (KBr) 1630 cm$^{-1}$; $^1$H NMR (CDCl$_3$) δ7.71 (m, 1H), 7.50 (m, 2H), 7.61 (m, 1H), 7.33 (m, 2H), 4.36 (d, 1H, J=11.2 Hz), 3.70 (m, 3H), 2.58 (m, 4H), 2.38 (m, 4H), 2.27 (s, 3H), 2.02 (m, 4H). MS m/z 317 (100, M$^+$), 217, 180, 139, 99, 70. Anal. (C$_{17}$H$_{23}$N$_3$OS)C, H, N.

(±)-3-[(4-Methylpiperazin-1-yl)methyl]-11-phenyl-5H,11H-pyrrolo [2,1-c][1,4]benzothiazepine (31). A solution of compound 39[20] (0.55 g, 2.0 mmol), paraformaldehyde (0.1 g) and 1-methylpiperazine dihydrochloride (0.52 g, 3.0 mmol) in CH$_3$OH (20 mL) was refluxed for 48 hours. After cooling, the mixture was diluted with water and made alkaline (pH 9–10) by dropwise addition of 1N NaOH. The oil formed was extracted with ethyl acetate. The organic layer was washed with water and dried. After evaporation of the solvent, the residue obtained was chromatographed (5% CH$_3$OH in CH$_2$Cl$_2$) to give the title compound 31 as a white solid (0.7 g, 91% yield): mp 161–162° C. (2-propanol); $^1$H NMR (CDCl$_3$) δ7.50–7.00 (m, 9H), 5.97 (s, 1H), 5.86 (d, 1H, J=3.5 Hz), 5.53 (d, 1H, J=3.5 Hz), 5.36 (AB q, 2H, J=14.5 Hz), 3.50 (AB q, 2H, J=13.5 Hz), 2.52 (m, 8H), 2.30 (s, 3H). Anal. (C$_{24}$H$_{27}$N$_3$S)C, H, N.

EXAMPLE 4

Procedure for the Preparation of Sulfoxides 15–18

This procedure is illustrated for the preparation of (±)-cis-1,11a-Dihydro-3H,5H,11H-thiazolo[4,3-c][1,4]benzothiazepine-5,11-dione 2-oxide (16). To a stirred and cooled (0° C.) solution of compound 5[15] (0.5 g, 2.0 mmol) in dry dichloromethane (5 mL)⁻80% 3-chloroperbenzoic acid (0.43 g, 2 mmol) in 8 mL of the same solvent was added dropwise over about 15 minutes. After an additional 2 hours at 0° C., the reaction mixture was filtered and the filter cake was rinsed with dichloromethane. The combined solution was washed twice with 5% aqueous K$_2$CO$_3$, dried, and evaporated to give the crude 16 (0.47 g, 89% yield), which solidified on trituration with hexane: mp 191–194° C. (benzene); IR (KBr) 1695, 1670 cm$^{-1}$; $^1$H NMR (CDCl$_3$) δ8.04 (m, 1H,), 7.55 (m, 3H), 5.75 (dd, 1H, J=13.1, 3.0 Hz), 5.14 (t, 1H, J=7.6 Hz), 3.91 (d, 1H, J=13.1 Hz), 3.72 (dd, 1H, J=14.6, 7.6 Hz), 3.23 (ddd, 1H, J=14.6, 7.6, 3.0 Hz). Anal. (C$_{11}$H$_9$NO$_3$S$_2$)C, H, N.

(±)-cis-2,3-Dihydro-7-methyl-5H-thiazolo[2,3-c][1,4]benzothiazepine-5,11 (11aH)-dione 1-Oxide (15). Starting from 4 (0.53 g, 2.0 mmol), the compound 15 (0.39 g, 73% yield) was obtained using an identical procedure as for 16: mp 211–212° C. (benzene); IR (KBr) 1690, 1670 cm$^{-1}$; $^1$H NMR (CDCl$_3$) δ7.79 (d, 1H, J=2.5 Hz), 7.38 (m, 2H), 5.25 (s, 1H), 4.52 (m, 1H), 3.40 (m, 1H), 3.10 (m, 1H), 2.47 (t, 3H). Anal. (C$_{12}$H$_{11}$NO$_3$S$_2$)C, H, N.

(±)-cis-7-Chloro-1,11a-dihydro-3H,5H,11H-thiazolo[4,3-c][1,4]benzothiazepine-5,11-dione 2-Oxide (17). Starting from 6 (0.57 g, 2.0 mmol), the compound 17 (0.41 g, 68% yield) was obtained using an identical procedure as for 16: mp 213–215° C. (benzene); IR (KBr) 1695, 1660 cm$^{-1}$; $^1$H NMR (CDCl$_3$) δ8.04 (d, 1H, J=2.7 Hz), 7.50 (m, 2H), 5.75 (dd, 1H, J=12.9, 2.9 Hz), 5.13 (t, 1H, J=7.8 Hz), 3.91 (d, 1H, J=13.0 Hz), 3.73 (dd, 1H, J=14.7, 7.2 Hz), 3.23 (ddd, 1H, J=14.7, 7.8, 2.9 Hz). Anal. (C$_{11}$H$_8$ClNO$_3$S$_2$)C, H, N.

(±)-cis-1,11a-Dihydro-7-methoxy-3H,5H,11H-thiazolo[4,3-c][1,4]benzothiazepine-5,11-dione 2-Oxide (18). Starting from 10 (0.56 g, 2.0 mmol), the compound 18 (0.42 g, 71% yield) was obtained using an identical procedure as for 16: mp 172–174° C. (benzene); IR (KBr) 1690, 1660 cm$^{-1}$; $^1$H NMR (CDCl$_3$) δ7.55 (d, 1H, J=2.7 Hz), 7.40 (d, 1H, J=8.3 Hz), 7.09 (dd, 1H, J=8.3, 2.7 Hz), 5.76 (dd, 1H, J=12.9, 2.8 Hz), 5.17 (t, 1H, J=7.6 Hz), 3.91 (d, 1H, J=12.9 Hz), 3.89 (s, 3H), 3.73 (dd, 1H, J=14.7, 7.1 Hz), 3.23 (ddd, 1 H, J=14.7, 7.6, 2.8 Hz). Anal. (C$_{12}$H$_{11}$NO$_4$S$_2$)C, H, N.

EXAMPLE 5

Integrase Assays

The HPLC purified oligonucleotides
AE117 (5'-ACTGCTAGAGATTTTCCACAC-3');
AE118 (5'-GTGTGGAAAATCTCTAGCAGT-3');
AE157 (5'-GAAAGCGACCGCGCC-3');
AE146 (5'-GGACGCCATAGCCCCGGCGCGGTCGCTTTC-3');
AE156 (5'-GTGTGGAAAATCTCTAGCAGGGGCTATGGCGTCC-3');
RM22M (5'-TACTGCTAGAGATTTTCCACAC-3'); and
RMAB2 (5'-GTGTGGAAAATCTCTAGCUGT-3') were purchased from Midland Certified Reagent Company (Midland, Tex.). An expression system for the wild-type integrase and the IN$^{50-212}$ (F185K) were obtained from the Laboratory of Molecular Biology, NIDDK, NIH, Bethesda, Md.

To analyze the extent of 3'-processing and strand transfer using 5'-end labeled substrates, AE118 was 5'-end labeled using T$_4$ polynucleotide kinase (Gibco BRL) and γ[$^{32}$P]-ATP (Dupont-NEN). To determine the extent of 30mer target strand generation during disintegration, AE157 was 5'-end labeled and annealed to AE156, AE146, and AE117. The kinase was heat-inactivated and AE117 was added to the same final concentration. The mixture was heated at 95° C., allowed to cool slowly to room temperature, and run through a G-25 Sephadex quick spin column (Boehringer Mannheim, Indianapolis, Ind.) to separate annealed double-stranded oligonucleotide from unincorporated label.

To analyze the extent of site-specific cleavage of 3'-end-labeled substrate by integrase, AE118 was 3'-end-labeled using γ[$^{32}$P]-cordycepin triphosphate (Dupont-NEN) and terminal transferase (Boehringer Mannheim). The transferase was heat-inactivated, and RM22M was added to the same final concentration. The mixture was heated at 95° C., allowed to cool slowly to room temperature, and run through a G-25 spin column as before.

To determine the extent of Schiff base formation, RMAB2 was 5'-end labeled and reacted with AE117 as described above. The uracil was removed from duplex oligonucleotide containing deoxyuridine by incubation of 40 μl of end-labeled DNA (500 nM stock solution) with 1 unit of uracil DNA glycosylase (Life Technologies, Inc.) for 90 minutes at 30 C. The reaction was then loaded on a G-25 Sephadex quick spin column to remove the unincorporated label and the uracil.

To determine the extent of 3'-processing and strand transfer, integrase was preincubated at a final concentration of 200 nM with the inhibitor in a reaction buffer (50 mM NaCl, 1 mM HEPES, pH 7.5, 50 μM EDTA, 50 μM dithiothreitol, 10% glycerol (w/v), 7.5 mM $MnCl_2$, 0.1 mg/ml bovine serum albumin, 10 mM 2-mercaptoethanol, 10% dimethyl sulfoxide, and 25 mM MOPS, pH 7.2) at 30° C. for 30 minutes. Then, 20 nM of the 5'-end $^{32}P$ labeled linear oligonucleotide substrate was added, and incubation was continued for an additional one hour. Reactions were quenched by the addition of an equal volume (16 μ) of loading dye (98% deionized formamide, 10 mM EDTA, 0.025% xylene cyanol and 0.025% bromophenol blue). An aliquot (5 μl) was electrophoresed on a denaturing 20% polyacrylamide gel (0.09 M tris-borate pH 8.3, 2 mM EDTA, 20% acrylamide, 8M urea).

Gels were dried, exposed in a PhosphorImager cassette, and analyzed using a Molecular Dynamics PhosphorImager (Sunnyvale, Calif.). Percent inhibition was calculated using the following equation:

$$\% I = 100 \times [1-(D-C)/(N-C)]$$

where C, N, and D are the fractions of 21-mer substrate converted to 19-mer (3'-processing product) or strand transfer products for DNA alone (C), DNA plus integrase (N), and integrase plus drug (D). All $IC_{50}$ values were determined by plotting the drug concentration versus percent inhibition, and determining the concentration which produced 50% inhibition.

To determine the effects of drugs on the choice of nucleophile in the 3'-processing, reactions were performed essentially as described above with a 3'-end labeled oligonucleotide. Disintegration reactions were performed as above with a Y oligonucleotide (i.e., the branched substrate in which the U5 end was "integrated" into target DNA).

EXAMPLE 6

HIV-1 Cell and Target-based Assays

The cell-based p24 attachment assay has been described in detail elsewhere.[33] Assays for activity against HIV-1 reverse transcriptase rAdT (template/primer) and rCdG (template/primer) using recombinant HIV-1 reverse transcriptase, have been previously described.[34] The substrate cleavage of recombinant HIV-1 protease in the presence of test compounds was quantified using an HPLC-based methodology with the artificial substrate Ala-Ser-Glu-Asn-Try-Pro-Ile-Val-amide (Multiple Peptide Systems, San Diego, Calif.) as has been previously described.[33,35]

EXAMPLE 7

Anti-HIV Assays in Cultured Cell Lines

The anti-HIV drug testing was performed at NCI based on a protocol described by Weislow et al.[36] All compounds were dissolved in dimethyl sulfoxide and diluted 1:100 in cell culture medium. Exponentially growing T4 lymphocytes (CEM cell line) were added at 5000 cells per well. Frozen virus stock solutions were thawed immediately before use, suspended in complete medium to yield the desired multiplicity of infection (m. o. i.≈0.1), and added to the microtiter wells, resulting in a 1:200 final dilution of the compound. Uninfected cells with the compound served as a toxicity control, and infected and uninfected cells without the compound served as basic controls.

Cultures were incubated at 37° C. in a 5% $CO_2$ atmosphere for 6 days. The tetrazolium salt, XTT was added to all wells, and cultures were incubated to allow formazan color development by viable cells. Individual wells were analyzed spectrophotometrically to quantitate formazan production, and in addition were viewed microscopically for detection of viable cells and confirmation of protective activity.

All positive control compounds for individual assays except AZTTP were obtained from the NCI chemical repository. The reference reagents for the individual assays were as follows:
  attachment: Farmatalia (NSC 65016)[29] and dextran sulfate (NSC 620255);
  reverse transcriptase inhibition: rAdT Template/primer-AZTEC (Sierra BioResearch, Tuscon, Ariz.), rCdG Template/primer-UC38 (NSC 629243);
  protease inhibition: KNI-272[31] (NSC 651714).

EXAMPLE 8

Identification of Anti-Integrase and Anti-Viral Compounds

The thiazepines of the present invention were tested for anti-integrase and anti-viral activity, and the results are shown in Table 1.

TABLE 1

Anti-HIV-1 Integrase Activities of Thiazepines 1–31

| Compd | $R_1$ | $R_2$ | $R_3$ | $R_4$ | $R_5$ | $R_6$ | —X—Y— | Z | 3'- Processing | 3'-end joining | $^a EC_{60}$ | $^b CC_{50}$ |
|---|---|---|---|---|---|---|---|---|---|---|---|---|
| 1 | H | H | | | | | —S—$CH_2$— | | 110 ± 12 | 146 ± 79 | 107 | >200 |
| 2 | H | Cl | | | | | —S—$CH_2$— | | 151; 105 | 120; 60 | >50 | >50 |
| 3 | H | Br | | | | | —S—$CH_2$— | | 58 ± 15 | 48 ± 18 | | |
| 4 | H | Me | | | | | —S—$CH_2$— | | 64 ± 47 | 55 ± 29 | | |

TABLE 1-continued

Anti-HIV-1 Integrase Activities of Thiazepines 1–31

|       |       |       |       |       |       |       |         |       | Integrase Assay $IC_{50}$ ($\mu$M) | | Cell data ($\mu$M) | |
|-------|-------|-------|-------|-------|-------|-------|---------|-------|------------|------------|------------|------------|
|       |       |       |       |       |       |       |         |       | 3'-Processing | 3'-end joining | $^a$EC$_{60}$ | $^b$CC$_{50}$ |
| Compd | R$_1$ | R$_2$ | R$_3$ | R$_4$ | R$_5$ | R$_6$ | —X—Y—   | Z     |            |            |            |            |
| 5     | H     | H     |       |       |       |       | —CH$_2$—S— |     | 208 ± 24   | 227 ± 104  | >200       | >200       |
| 6     | H     | Cl    |       |       |       |       | —CH$_2$—S— |     | 158; 111   | 160; 110   | >100       | >100       |
| 7     | H     | Br    |       |       |       |       | —CH$_2$—S— |     | 87 ± 24    | 74 ± 32    | >200       | >200       |
| 8     | H     | Me    |       |       |       |       | —CH$_2$—S— |     | 52         | 63         | NR         | 35         |
| 9     | NO$_2$| H     |       |       |       |       | —CH$_2$—S— |     | 90 ± 27    | 100 ± 36   | >50        | >50        |
| 10    | H     | OMe   |       |       |       |       | —CH$_2$—S— |     | 155; 275   | 155; 245   | >200       | >200       |
| 11    | OMe   | OMe   |       |       |       |       | —CH$_2$—S— |     | 670; 630   | 333; 330   | >50        | >50        |
| 12    | H     | H     |       |       |       |       | —CH$_2$—O— |     | >333       | >333       |            |            |
| 13    | OMe   | OMe   |       |       |       |       | —(CH$_2$)$_2$— | | >1000      | >1000      | >200       | >200       |
| 14    | H     | H     |       |       |       |       | —(CH$_2$)$_3$— | | 406; 495   | 343 ± 109  | >200       | >200       |
| 15    | H     | Me    |       |       |       |       | —S(O)—CH$_2$— | | 590 ± 350  | 590 ± 350  | >100       | >100       |
| 16    | H     | H     |       |       |       |       | —CH$_2$—S(O)— | | 200; 185   | 215; 222   |            |            |
| 17    | H     | Cl    |       |       |       |       | —CH$_2$—S(O)— | | 260; 215   | 280; 200   |            |            |
| 18    | H     | OMe   |       |       |       |       | —CH$_2$—S(O)— | | 84.5       | 142        |            |            |
| 19    |       |       |       |       |       |       | —S—CH$_2$— |     | 40 ± 10    | 47 ± 6     | 60         | >316       |
| 20    |       |       |       |       |       |       | —CH$_2$—S |     | 92 ± 30    | 100 ± 40   | 280        | >316       |
| 21    | H     | H     | H     | OAc   | H     |       | —(CH$_2$)$_2$— | | >1000      | >1000      | >200       | >200       |
| 22    | H     | H     | H     | OMe   | H     |       | —(CH$_2$)$_2$— | | >1000      | >1000      | >200       | >200       |
| 23    | H     | H     | Ph    | H     | H     |       | —CH$_2$—S— |     | 372; 111   | 376; 288   |            |            |
| 24    | OMe   | OMe   | H     | H     | H     |       | —(CH$_2$)$_2$— | | >1000      | >1000      | >200       | >200       |
| 25    | H     | H     | H     | OH    | H     |       | —(CH$_2$)$_2$— | | >1000      | >1000      | >200       | >200       |
| 26    | H     | H     | H     | OH    | Ph    |       | —(CH$_2$)$_2$— | | >1000      | >1000      |            |            |
| 27    | H     | H     | H     | H     | N(CH$_2$CH$_2$)$_2$NMe | —(CH$_2$)$_2$— | | >1000 | >1000 | >125 | >125 |
| 28    |       |       |       |       |       | H     |         | >CO   | 590        | 300        | 146        | >200       |
| 29    |       |       |       |       |       | H     |         | >CHCO$_2$Et | >1000 | >1000 |            |            |
| 30    |       |       |       |       |       | CH$_2$NMe$_2$ |  | >CHC$_6$H$_4$-pF | >1000 | >1000 |     |            |
| 31    |       |       |       |       |       | CH$_2$N(CH$_2$CH$_2$)$_2$NMe | | >CHPh | >1000 | >1000 |       |            |

$^a$EC$_{60}$: 50% effective concentration
$^b$CC$_{50}$: 50% cytotoxic concentration Benzothiazepine 1 was identified as an IN inhibitor (IC$_{50}$ values for 3'-processing and 3'-end joining: 110 and 146 $\mu$M, respectively) by showing it to have antiviral activity in the NCI Antiviral Drug Screen against CEM cells (Example 7). Compound 1 with a therapeutic index (TI=CC$_{50}$/EC$_{50}$) value of >1.8 (50% effective concentration [EC$_{50}$] value of 107±26 and a 50% cytotoxic concentration [CC$_{50}$] value of >200 $\mu$M) is moderately active in HIV-1 infected CEM cells. This compound was also found to be relatively non-cytotoxic, such that it would more specifically affect HIV than normal host cells. Hence once the inventors recognized the anti-integrase activity of this compound, benzothiazepine 1 served as a "lead" compound for the design and testing of more potent derivatives.

In order to establish a structure-activity relationship, 30 analogs were prepared and tested in an assay specific for IN as well as against HIV-1-infected CEM cells (see Table 1). Several modifications were made to determine the biological effect of each ring and the substituents. The first modifications were aimed at the A and B rings (compounds 1–18). In a second class of compounds, an extra benzene ring was added, and the effect of the position of the sulfur in the thiazolo ring was analyzed (19 and 20). The third group contains substitutions on all the rings (21–27) and the last group (28–31) was designed to determine the effect of the thiazepine ring system on biological activity.

As illustrated in Table 1, the chloro-, bromo-, and the methyl-substituted derivatives 2–4, exhibited potency similar to the parent compound 1 against purified IN. Compound 2 was tested for antiviral activity only at 50 $\mu$M and lower. Comparable results were obtained when sulfur was moved to position 10 as in compounds 5–11 (Table 1). However, the removal of sulfur (compounds 12–14) substantially reduced anti-IN and antiviral activities. Oxidation of the sulfur atom also generally reduced potency (compounds 15–18), but with compound 18 showing the best anti-IN activity. Both of the naphtho-derivatives 19 and 20 showed antiviral as well as anti-IN activity. Compound 19 with an IC$_{50}$ value of 40 $\mu$M against IN was more active than the parent compound 1 against HIV-1 infected cells. Compound 19 with a therapeutic index (TI) value of >5 was the best in this series (EC$_{50}$:60 and CC$_{50}$:>316 $\mu$M). Moreover, the naphthalene substituted compound 20 was active both against purified IN (IC$_{50}$ values of 92 and 100 $\mu$M against 3'-processing and strand transfer, respectively) and HIV-1 infected cells ($EC_{50}$: 279–286 and $IC_{50}$:>316 μM). Other modifications of the ring system (compounds 21–31) reduced both antiviral and anti-IN activities.

In particular embodiments, but without limiting the invention, an EC50 of 200 μM or less identifies a compound that is particularly suitable for further investigation. A $CC_{50}$ as high as possible is desired, for example at least 100, 200, 300 or even 1000. A TI value of at least 1 (for example 1.5 or greater) also helps identify compounds for further investigation.

EXAMPLE 9

Role of Divalent Metals

Divalent metal ions, such as $Mn^{+2}$ or $Mg^{+2}$, coordinate with the acidic residues (D, D, E) of IN's active site.[27] Metals are involved in the catalytic functioning because the enzyme is unable to perform 3' processing and strand transfer without $Mn^{+2}$ or $Mg^{+2}$. Previous studies have implied that hydroxylated aromatic inhibitors of IN are potentially metal chelators.[8,9,28] Thus, chelating metals at the active site of IN has been proposed to be responsible for the inhibition of IN function. However, hydroxylated aromatics are generally active only when $Mn^{+2}$ is used as a cofactor.[8].

Figure 2:
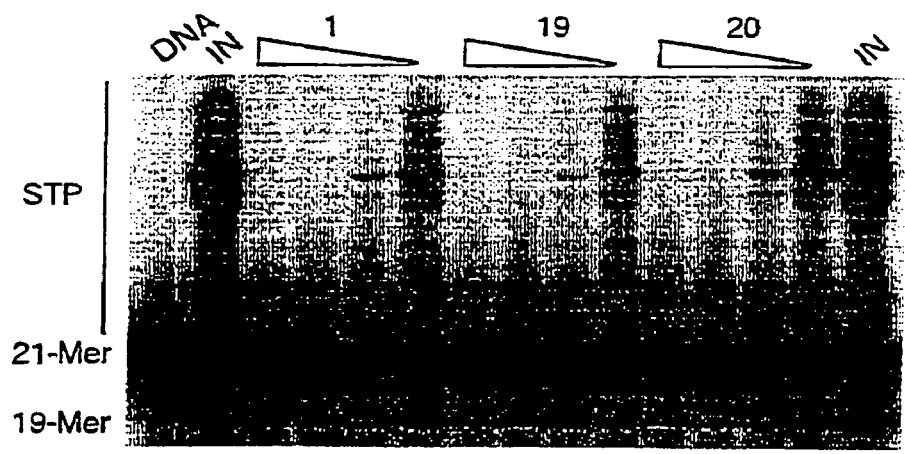
FIGS. 2 and 3 show concentration dependent inhibition of HIV-1 IN by thiazolothiazepines 1, 19, and 20 using $Mn^{+2}$ (FIG. 2) and $Mg^{+2}$ (FIG. 3) as a cofactor. Lane 1, DNA alone, lanes 2 and 15 DNA and integrase, lanes 3–6, 7–10, 11–14 DNA, integrase, and compounds 1, 19, and 20 at 1000, 333, 111, and 37 μM, respectively. See Table 1 for compound identifiers 1, 19, 20.
Figure 3:
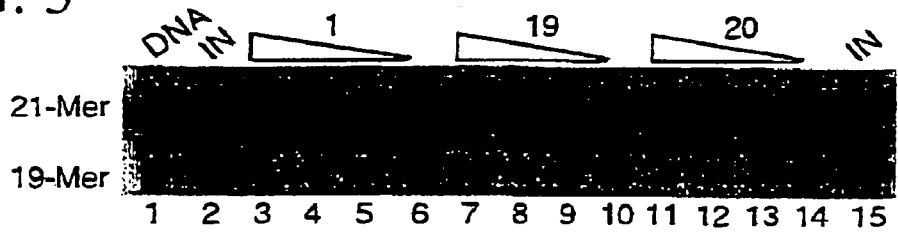

In contrast, the thiazolothiazepines of the present invention are equally active in $Mg^{+2}$-based assays. FIG. 1 shows a representative gel comparing the inhibition of IN in the presence of $Mn^{+2}$ or $Mg^{+2}$. A 21-mer oligonucleotide corresponding to the last 21 bases on the HIV-1 viral DNA in the U5 region of long terminal repeat (LTR) was radiolabeled with $^{32}P$. This is shown in the FIGS. 2 and 3 as a band corresponding to DNA alone. Integrase will cleave the last two bases of this DNA in the presence of $Mn^{+2}$ or $Mg^{+2}$ to give a 19-mer DNA substrate (lane 2) which runs faster on the gel and is indicated as 19-mer on the Figures. When an inhibitor is added this process is blocked, therefore the original 21-mer DNA would not be cut. When an inhibitor is added at various concentrations, percent inhibition at every concentration will be calculated by quantification of the intensity of each band using an Imagequant program.

The gels are run using polyacrylamide according to the standard procedures. Upon completion of electrophoresis run, the gels are dried and exposed to a phosphorimager cassette. The cassettes are analyzed by the phosphorimager, and the bands are shown on a computer screen. The intensity of each band is quantitated, plotted against concentrations of drugs, and the $IC_{50}$ values are calculated from the graphs.

Compounds 1, 19 and 20 were active in the presence of $Mg^{+2}$ within the same concentration range as in $Mn^{+2}$, thus indicating that these compounds differ from hydroxylated aromatics and perhaps act at different sites on IN. Inhibition of IN in the presence of $Mg^{+2}$ by thiazolothiazepines sets this class of compounds apart from other IN inhibitors. The activity in $Mg^{+2}$ is believed to be related to the antiviral activity of the thiazolothiazepines and derivatives, because $Mg^{+2}$ has been proposed to be the metal used in vivo by IN. Hence compounds having activity that is inhibited in the presence of $Mg^{2+}$ would be expected to have less antiviral activity in the presence of the viral $Mg^{2+}$.

EXAMPLE 10

Selectivity of Compounds

The selectivity of compounds 1,19, and 20 was examined against other sites on the HIV replication cycle. Assays for activity against HIV-1 reverse transcriptase rAdT (template/primer) and rCdG (template/primer) using recombinant HIV-1 reverse transcriptase (from ABL Basic Research NCI-FCRDC, Frederick, Md.) have been previously described.[30] A cell-based viral p24 attachment assay, and a nucleoprotein zinc finger assay, have also been described in detail in Rice et al.[33] The substrate cleavage of recombinant HIV-1 protease in the presence of test compounds was quantified using an HPLC-based methodology with the artificial substrate Ala-Ser-Glu-Asn-Tyr-Pro-Ile-Val-amide (Multiple Peptide Systems, San Diege, Calif.) as previously described.[30].

When tested against reverse transcriptase, protease, virus attachment, or nucleocapsid protein zinc fingers, none of the compounds exhibited any detectable activities at 100 μM, indicating moderate selectivity against IN. Thus, thiazolothiazepines are a group of selective inhibitors of HIV IN, that can serve as therapeutic compounds or lead compounds in the development of analogs and other derivatives.

The fact that thiazolothiazepines are equally potent in $Mg^{+2}$- and $Mn^{+2}$-based assays indicates that the IN binding site of these compounds differs from the binding site of previously reported inhibitors. Testing these compounds against other viral proteins (reverse transcriptase, protease, virus attachment, or nucleocapsid zinc fingers) shows selectivity of the compounds for IN, as compared to other steps in the retroviral life cycle. Another advantage of this class of compounds is that they are amenable for preparation of chemical libraries using recent advances in combinatorial chemistry, and can be used as novel lead compounds for designing drugs against IN and HIV replication.

Reference Reagents for Mechanistic and Target-based Assays. All positive control compounds for individual assays except AZTTP were obtained from the NCI chemical repository. The reference reagents for the individual assays are as follows:

attachment: Farmitalia (NSC 65016) and dextran sulfate (NSC 620255);

reverse transcriptase inhibition: rAdT Template/primer-AZTEC (Sierra BioResearch, Tuscon, Ariz.), rCdG Template/primer-UC38 (NSC 629243);

protease inhibition: KNI-272 (NSC 651714);

IN inhibitor: ISIS 5320 (NSC 665353) and DIBA-1 (NSC 654077) a NCp7 Zn finger inhibitor.

EXAMPLE 11

Methods of Treatment

The present invention includes a treatment for HIV disease and associated diseases, in a subject such as an animal, for example a rat or human. The method includes administering the compound of the present invention, or a combination of the compound and one or more other pharmaceutical agents, to the subject in a pharmaceutically compatible carrier and in an amount effective to inhibit the development or progression of HIV disease. Although the treatment can be used prophylactically in any patient in a demographic group at significant risk for such diseases, subjects can also be selected using more specific criteria, such as a definitive diagnosis of the condition.

The vehicle in which the drug is delivered can include pharmaceutically acceptable compositions of the drugs, using methods well known to those with skill in the art. Any of the common carriers, such as sterile saline or glucose solution, can be utilized with the drugs provided by the invention. Routes of administration include but are not limited to oral and parenteral rountes, such as intravenous (iv), intraperitoneal (ip), rectal, topical, ophthalmic, nasal, and transdermal.

The drugs may be administered intravenously in any conventional medium for intravenous injection, such as an aqueous saline medium, or in blood plasma medium. The medium may also contain conventional pharmaceutical adjunct materials such as, for example, pharmaceutically acceptable salts to adjust the osmotic pressure, lipid carriers such as cyclodextrins, proteins such as serum albumin, hydrophilic agents such as methyl cellulose, detergents, buffers, preservatives and the like. A more complete explanation of parenteral pharmaceutical carriers can be found in *Remington: The Science and Practice of Pharmacy* (19$^{th}$ Edition, 1995) in chapter 95.

Embodiments of other pharmaceutical compositions can be prepared with conventional pharmaceutically acceptable carriers, adjuvants and counterions as would be known to those of skill in the art. The compositions are preferably in the form of a unit dose in solid, semi-solid and liquid dosage forms such as tablets, pills, powders, liquid solutions or suspensions.

The compounds of the present invention are ideally administered as soon as possible after potential or actual exposure to HIV infection. For example, once HIV infection has been confirmed by laboratory tests, a therapeutically effective amount of the drug is administered. The dose can be given by frequent bolus administration.

Therapeutically effective doses of the compounds of the present invention can be determined by one of skill in the art, with a goal of achieving tissue concentrations that are at least as high as the $IC_{50}$ of each drug tested in the foregoing examples. The low toxicity of the compound makes it possible to administer high doses, for example 100 mg/kg, although doses of 10 mg/kg, 20 mg/kg, 30 mg/kg or more are contemplated. An example of such a dosage range is 0.1 to 200 mg/kg body weight orally in single or divided doses. Another example of a dosage range is 1.0 to 100 mg/kg body weight orally in single or divided doses. For oral administration, the compositions are, for example, provided in the form of a tablet containing 1.0 to 1000 mg of the active ingredient, particularly 1, 5, 10, 15, 20, 25, 50, 100, 200, 400, 500, 600, and 1000 mg of the active ingredient for the symptomatic adjustment of the dosage to the subject being treated.

The specific dose level and frequency of dosage for any particular subject may be varied and will depend upon a variety of factors, including the activity of the specific compound, the metabolic stability and length of action of that compound, the age, body weight, general health, sex, diet, mode and time of administration, rate of excretion, drug combination, and severity of the condition of the host undergoing therapy.

The pharmaceutical compositions can be used in the treatment of a variety of retroviral diseases caused by infection with retroviruses that require integrase activity for infection and viral replication. Examples of such diseases include HIV-1, HIV-2, the simian immunodeficiency virus (SIV), the feline immunodeficiency virus (FIV), HTLV-1, HTLV-2, spumavirus (human foamy virus) and feline infectious leukemia.

EXAMPLE 12

Combination Therapy

The present invention also includes combinations of HIV integrase inhibitor compounds with one or more agents useful in the treatment of HIV disease. For example, the compounds of this invention may be administered, whether before or after exposure to the virus, in combination with effective doses of other anti-virals, immunomodulators, anti-infectives, or vaccines. The term "administration" refers to both concurrent and sequential administration of the active agents.

Example of antivirals that can be used in combination with the integrase inhibitors of the invention are: AL-721 (from Ethigen of Los Angeles, Calif.), recombinant human interferon beta (from Triton Biosciences of Alameda, Calif.), Acemannan (from Carrington Labs of Irving, Tex.), gangiclovir (from Syntex of Palo alto, Calif.), didehydrodeoxythymidine or d4T (from Bristol-Myers-Squibb), EL10 (from Elan Corp. of Gainesville, Ga.), dideoxycytidine or ddC (from Hoffman-LaRoche), Novapren (from Novaferon labs, Inc. of Akron, Ohio), zidovudine or AZT (from Burroughs Wellcome), ribaririn (from Viratek of Costa Mesa, Calif.), alpha interferon and acyclovir (from Burroughs Wellcome), Indinavir (from Merck & Co.), 3TC (from Glaxo Wellcome), Ritonavir (from Abbott), Saquinavir (from Hoffmann-LaRoche), and others.

Examples of immuno-modulators that can be used in combination with the integrase inhibitors of the invention are AS-101 (Wyeth-Ayerst Labs.), bropirimine (Upjohn), gamma interferon (Genentech), GM-CSF (Genetics Institute), IL-2 (Cetus or Hoffman-LaRoche), human immune globulin (Cutter Biological), IMREG (from Imreg of New Orleans, La.), SK&F106528, and TNF (Genentech).

Examples of some anti-infectives with which the integrase inhibitors can be used include clindamycin with primaquine (from Upjohn, for the treatment of pneumocystis pneumonia), fluconazlone (from Pfizer for the treatment of cryptococcal meningitis or candidiasis), nystatin, pentamidine, trimethaprimsulfamethoxazole, and many others.

The combination therapies are of course not limited to the lists provided in these examples, but includes any composition for the treatment of HIV disease (including treatment of AIDS).

EXAMPLE 13

Obtaining HIV Integrase Inhibitors by Combinatorial Chemistry

Combinatorial chemistry allows generation of large numbers of unique molecules with a small number of chemical reactions. Rather than using the traditional approach of synthesizing novel compounds one at a time, compounds are synthesized by performing chemical reactions in stages, and reacting all of the molecules formed in stage n-1 with each reactant in stage n. Such techniques can be used to obtain analogs and other variants of the thiazepines of the present invention, and to test them for anti-integrase activity.

In view of the many possible embodiments to which the principles of the invention may be applied, it should be recognized that the illustrated embodiments are only particular examples of the invention and should not be taken as a limitation on the scope of the invention. Rather, the scope of the invention is defined by the following claims. We therefore claim as our invention all that comes within the scope and spirit of these claims.

REFERENCES

1) Brown, P. O. *Integration*; Cold Spring Harbor Press: Cold Spring Harbor, 1998.
2) Mazumder, A.; Neamati, N.; Sunder, S.; Owen, J.; Pommier, Y. *Retroviral Integrase: A Novel Target in Antiviral*

*Development; Basic In Vitro Assays with the Purified Enzyme*; Mazumder, A.; Neamati, N.; Sunder, S.; Owen, J.; Pommier, Y., Ed.; The Humana Press, Inc.: Totowa, N.J., 1998, pp 1998.

3) Chow, S. A. In vitro assays for activities of retroviral integrase. *Methods* 1997, 12, 306–17.

4) Chow, S. A.; Vincent, K. A.; Ellison, V.; Brown, P. O. Reversal of integration and DNA splicing mediated by integrase of human immunodeficiency virus. *Science* 1992, 255, 723–6.

5) Pommier, Y.; Pilon, A.; Bajaj, K.; Mazumder, A.; Neamati, N. HIV-1 integrase as a target for antiviral drugs. *Antiviral Chem Chemother* 1997, 8, 483–503.

6) Neamati, N.; Sunder, S.; Pommier, Y. Design and discovery of HIV-1 integrase inhibitors. *Drug Discovery Today* 1997, 2, 487–498.

7) Stanwell, C.; Ye, B.; Yuspa, S. H.; Burke, T. R., Jr. Cell protein crosslinking by erbstatin and related compounds. *Biochem Pharmacol* 1996, 52, 475–80.

8) Neamati, N.; Hong, H.; Owen, J. M.; Sunder, S.; Winslow, H. E.; Christensen, J. L.; Zhao, H.; Burke, J. T. R.; Milne, G. W. A.; Pommier, Y. Salicylhydrazine-containing inhibitors of HIV-1 integrase: implication for a selective chelation in the integrase active site. *J Med Chem* 1998, 41, 3202–3209.

9) Neamati, N.; Hong, H.; Mazumder, A.; Wang, S.; Sunder, S.; Nicklaus, M. C.; Milne, G. W.; Proksa, B.; Pommier, Y. Depsides and depsidones as inhibitors of HIV-1 integrase: discovery of novel inhibitors through 3D database searching. *J Med Chem* 1997, 40, 942–51.

10) Nicklaus, M. C.; Neamati, N.; Hong, H.; Mazumder, A.; Sunder, S.; Chen, J.; Milne, G. W.; Pommier, Y. HIV-1 integrase pharmacophore: discovery of inhibitors through three-dimensional database searching. *J Med Chem* 1997, 40, 920–9.

11) Lubkowski, J.; Yang, F.; Alexandratos, J.; Wlodawer, A.; Zhao, H.; Burke, T. R., Jr.; Neamati, N.; Pommier, Y.; Merkel, G.; Skalka, A. M. Structure of the catalytic domain of avian sarcoma virus integrase with a bound HIV-1 integrase-targeted inhibitor. *Proc Natl Acad Sci USA* 1998, 95, 4831–6.

12) Neamati, N.; Mazumder, A.; Zhao, H.; Sunder, S.; Burke, T. R., Jr.; Schultz, R. J.; Pommier, Y. Diarylsulfones, a novel class of human immunodeficiency virus type 1 integrase inhibitors. *Antimicrob Agents Chemother* 1997, 41, 385–93.

13) Neamati, N.; Mazumder, A.; Sunder, S.; Owen, J. M.; Schultz, R. J.;
Pommier, Y. 2-Mercaptobenzenesulfonamides as novel class of human immunodeficiency type 1 (HIV-1) integrase and HIV-1 replication. *Antimicrob Agents Chemother* 1997, 8, 485–495.

14) Garofalo, A.; Balconi, G.; Botta, M.; Corelli, F.; D'Incalci, M.; Fabrizi, G.; Fiorini, I.; Lamba, D.; Nacci, V. Thioanalogues of anti-tumor antibiotics. II. Synthesis and preliminary in vitro cytotoxicity evaluation of tricyclic [1,4]benzothiazepine derivatives. *Eur J Med Chem* 1993, 29, 213–220.

15) Nacci, V.; Garofalo, A.; Anzini, M. Thioanalogues of antitumor antibiotics. I. Synthesis of 7,8 disubstituted 5,11-dioxo-1,2,3,11a-tetrahydro-5H,11H and 5-oxo-2,3,11,11a-tetrahydro-1H,5H-pyrrolo[2,1-c][1,4]benzothiazepine. *Farmaco* 1989, 44, 423–433.

16) Nacci, V.; Garofalo, A.; Fiorini, I. Polycondensed heterocycles. II. A new preparative route to 11-oxo-5H,11H-pyrrolo[2,1-c][1,4]benzothiazepine. *J Heterocycl Chem* 1986, 23, 769–773.

17) Garofalo, A.; Nacci, V.; Corelli, F.; Campiani, G. Polycondensed heterocycles. V. Synthesis of 5H,11H-pyrrolo[2,1-c][1,4]benzothiazepine. *Heterocycles* 1990, 31, 1291–1300.

18) Garofalo, A.; Campiani, G.; Ciani, S. M.; Fiorini, I.; Nacci, V. Polycondensed heterocycles. IX. Pyrrolo[2,1-c][1,4]benzothiazepines. Synthesis of 3-(dimethylamino)methyl derivatives. *Tetrahedron* 1996, 52, 7745–7754.

19) Garofalo, A.; Campiani, G.; Nacci, V.; Fiorini, I. Polycondensed heterocycles. VIII. Synthesis of 11-aryl-5H,11H-pyrrolo[2,1-c][1,4]benzothiazepines by Pummerer rearrangement-cyclization reaction. *Heterocycles* 1992, 34, 51–60.

20) Archer, S.; Miller, J. K.; Rej, R.; Periana, C.; Fricker, L. Ring-hydroxylated analogues of lucantone as antitumor agents. *J Med Chem* 1982, 25, 220–227.

21) Katz, L.; Karger, L. S.; Schroeder, W.; Cohen, M. S. Hydrazine derivatives. I. Benzalthio- and bisbenzaldithiosalicylhydrazides. *J Org Chem* 1953, 18, 1380–1402.

22) Pendergast, W.; Dickerson, S. H.; Dev, I. K.; Ferone, R.; Duch, D. S.; Smith, G. K. Benzo[f]quinazoline inhibitors of thymidylate synthase: methyleneamino-linked aroylglutamate derivatives. *J Med Chem* 1994, 37, 838–844.

23) Guise, G. B.; Ollis, W. D.; Peacock, J. E.; Stephanatou, J. S.; Stoddart, J. F. Dithiosalicylides and trithiosalicylides. Their conformational behavior in solution. *Tetrahedron Lett* 1980, 21, 4203–4206.

24) Vitali, T.; Mossini, F.; Plazzi, P. V. Sintesi ed attivita' antifungine di bis(3-carbossiamido-2-naftil)disolfuri e di nafto[3,2-d]isotiazolin-3-oni. Il *Farmaco Ed Sc* 1974, 29, 27–36.

25) Lalezari, I.; Schwartz, E. L. Synthesis and antineoplastic activity of 5Aryl-2,3-dihydropyrrolo[2,1-b]thiazole-6,7-dimethanol 6,7-bis(isopropylcarbamates). *J Med Chem* 1988, 31, 1427–1429.

26) Falorni, M.; Conti, S.; Giacomelli, G.; Cossu, S.; F., S. Optically active 4-oxaproline derivatives: new useful chiral synthons derived from serine and threonine. *Tetrahedron: Asymmetry* 1995, 6, 287–294.

27) Goldgur, Y.; Dyda, F.; Hickman, A. B.; Jenkins, T. M.; Craigie, R.; Davies, D. R. Three new structures of the core domain of HIV-1 integrase: An active site that binds magnesium. *Proc Natl Acad Sci USA* 1998, 95, 9150–4.

28) Fesen, M. R.; Pommier, Y.; Leteurtre, F.; Hiroguchi, S.; Yung, J.; Kohn, K. W. Inhibition of HIV-1 integrase by flavones, caffeic acid phenethyl ester (CAPE) and related compounds. *Biochem Pharmacol* 1994, 48, 595–608.

29) Clanton, D. J.; Buckheit, R. W., Jr.; Terpening, S. J.; Kiser, R.; Mongelli, N.; Borgia, A. L.; Schultz, R.; Narayanan, V.; Bader, J. P.; Rice, W. G. Novel sulfonated and phosphonated analogs of distamycin which inhibit the replication of HIV. *Antiviral Res* 1995, 27, 335–54.

30) Bader, J. P.; McMahon, J. B.; Schultz, R. J.; Narayanan, V. L.; Pierce, J. B.; Harrison, W. A.; Weislow, O. S.; Midelfort, C. F.; Stinson, S. F.; Boyd, M. R. Oxathiin carboxanilide, a potent inhibitor of human immunodeficiency virus reproduction. *Proc Natl Acad Sci USA* 1991, 88, 6740–4.

31) Kageyama, S.; Mimoto, T.; Murakawa, Y.; Nomizu, M.; Ford, H., Jr.; Shirasaka, T.; Gulnik, S.; Erickson, J.; Takada, K.; Hayashi, H.; et al. In vitro anti-human immunodeficiency virus (HIV) activities of transition state mimetic HIV protease inhibitors containing allophenylnorstatine. *Antimicrob Agents Chemother* 1993, 37, 810–7.

32) Buckheit, R. W., Jr.; Roberson, J. L.; Lackman-Smith, C.; Wyatt, J. R.; Vickers, T. A.; Ecker, D. J. Potent and specific inhibition of HIV envelope-mediated cell fusion and virus binding by G quartet-forming oligonucleotide (ISIS 5320). *AIDS Res Hum Retroviruses* 1994, 10, 1497–506.

33) Rice, W. G.; Supko, J. G.; Malspeis, L.; Buckheit, R. W., Jr.; Clanton, D.; Bu, M.; Graham, L.; Schaeffer, C. A.; Turpin, J. A.; Domagala, J.; et al. Inhibitors of HIV nucleocapsid protein zinc fingers as candidates for the treatment of AIDS. *Science* 1995, 270, 1194–7.

34) Turpin, J. A.; Terpening, S. J.; Schaeffer, C. A.; Yu, G.; Glover, C. J.; Felsted, R. L.; Sausville, E. A.; Rice, W. G. Inhibitors of human immunodeficiency virus type 1 zinc fingers prevent normal processing of gag precursors and result in the release of noninfectious virus particles. *J Virol* 1996, 70, 6180–9.

35) Rice, W. G.; Baker, D. C.; Schaeffer, C. A.; Graham, L.; Bu, M.; Terpening, S.; Clanton, D.; Schultz, R.; Bader, J. P.; Buckheit, R. W., Jr.; Field, L.; Singh, P. K.; Turpin, J. A. Inhibition of multiple phases of human immunodeficiency virus type 1 replication by a dithiane compound that attacks the conserved zinc fingers of retroviral nucleocapsid proteins. *Antimicrob Agents Chemother* 1997, 41, 419–26.

36) Weislow, O. W.; Kiser, R.; Fine, D.; Bader, J.; Shoemaker, R. H.; Boyd, M. R. New soluble-formazan assay for HIV-1 cytopathic effects: application to high-flux screening of synthetic and natural products for AIDS antiviral activity. *J Natl Cancer Inst* 1989, 81, 577–586.

We claim:

1. A compound having the following formula, or a pharmaceutically acceptable salt thereof:

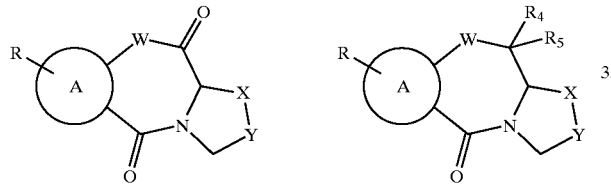

wherein A is benzene or naphthalene;
R is one or more of halogen or $NO_2$;
X—Y is $CH_2$—S, S—$CH_2$, $CH_2$—O, $CH_2$—S(O), S(O)—$CH_2$, $CH_2$—$CH_2$, $CH_2$—$CH_2$—$CH_2$, or $CH_2CH_2$—$CH_2$—$CH_2$;
$R_3$ is H or phenyl;
$R_4$ is H or hydroxy;
$R_5$ is H, phenyl, -alkyl-$NH_2$, —NH-alkyl, or —N(alkyl)$_2$; and
W is S
or wherein the compound is

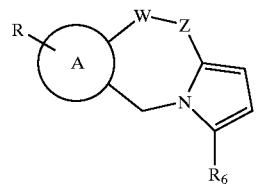

wherein
A is benzene or naphthalene and
R is one or more of halogen or $NO_2$;
$R_6$ is H, unsubstituted alkyl or amine, or alkyl or amine substituted with at least one substituent selected from halogen, alkyl, alkoxy, alkylthio, trifluoromethyl, acyloxy, hydroxy, mercapto, carboxy, aryloxy, aryl, arylalkyl, amino, alkylamino, dialkylamino, morpholino, piperidino, pyrrolidin-1-yl, or piperazin-1-yl;
W is S; and
Z is S, O, $CH_2$, $CH_2CH_2$, C=O, —$CHCO_2CH_2CH_3$, —$CHC_6H_4$-pF, or —$CHC_6H_5$.

2. A compound having the following formula, or a pharmaceutically acceptable salt thereof, wherein the compound is:

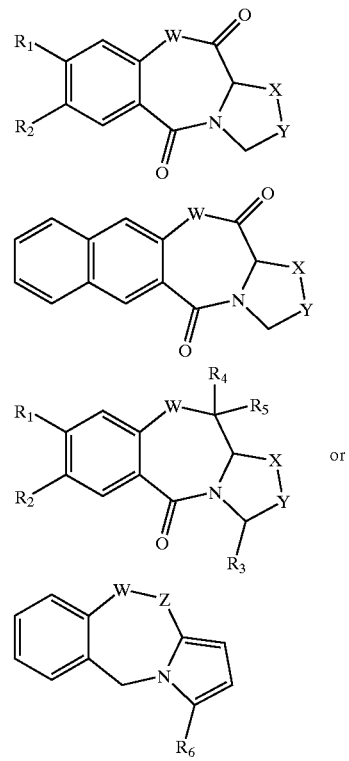

wherein
X—Y is S—$CH_2$, $CH_2$—S, S(O)—$CH_2$, $CH_2$—S(O), or $CH_2CH_2$;
Z is S, O, $CH_2$, $CH_2CH_2$, C=O, —$CHCO_2CH_2CH_3$, —$CHC_6H_4$-pF, or —$CHC_6H_5$;
W is S;
$R_1$ is H, halogen, lower alkyl, lower alkoxy, or $NO_2$;
$R_2$ is H, halogen, lower alkyl or lower alkoxy;
$R_3$ is H;
$R_4$ is hydroxy or H;
$R_5$ is phenyl or $N(CH_2CH_2)_2NCH_3$; and
$R_6$ is $CH_2N(CH_2CH_2)_2NCH_3$,
provided that $R_1$ and $R_2$ are not both H or not both alkoxy.

3. The compound of claim 2, wherein the compound is

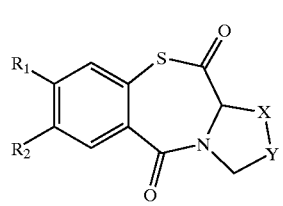

and $R_1$ is H or $NO_2$;
$R_2$ is H, halogen, lower alkyl or lower alkoxy;
provided that $R_1$ and $R_2$ are not both H or not both alkoxy.

4. The compound of claim 2, wherein
$R_1$ is H, $R_2$ is Cl, X—Y is S—$CH_2$; or
$R_1$ is H, $R_2$ is Br, X—Y is S—$CH_2$; or
$R_1$ is H, $R_2$ is $CH_3$, X—Y is S—$CH_2$; or
$R_1$ is H, $R_2$ is Cl, X—Y is $CH_2$—S; or
$R_1$ is H, $R_2$ is Br, X—Y is $CH_2$—S; or
$R_1$ is H, $R_2$ is $CH_3$, X—Y is $CH_2$—S; or
$R_1$ is $NO_2$, $R_2$ is H, X—Y is $CH_2$—S; or
$R_1$ is H, $R_2$ is $OCH_3$, X—Y is $CH_2$—S; or
$R_1$ is H, $R_2$ is $CH_3$, X—Y is S(O)—$CH_2$; or
$R_1$ is H, $R_2$ is Cl, X—Y is $CH_2$—S(O); or
$R_1$ is H, $R_2$ is $OCH_3$, X—Y is $CH_2$—S(O).

5. The compound of claim 2, wherein the compound is

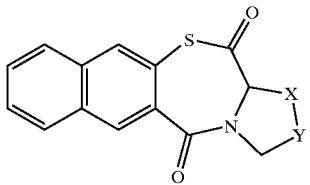

and X—Y is S—$CH_2$ or $CH_2$—S.

6. The compound of claim 2, wherein X—Y is S—$CH_2$.

7. A compound having the following formula, or a pharmaceutically acceptable salt thereof, wherein the compound is:

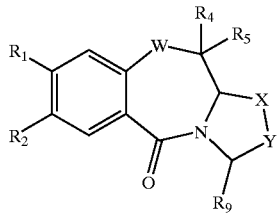

and $R_1$, $R_2$ and $R_3$ are H, $R_4$ is OH or H;
W is S;
$R_5$ is Ph or $N(CH_2CH_2)_2NCH_3$; and
X—Y is $CH_2$—$CH_2$.

8. The compound of claim 2, wherein the compound is

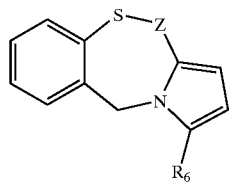

and $R_6$ is $CH_2N(CH_2CH_2)_2NCH_3$.

9. A pharmaceutical composition comprising the compound of claim 1, or the pharmaceutically acceptable salt, and a pharmaceutically acceptable carrier.

10. A pharmaceutical composition comprising the compound of claim 2, or the pharmaceutically acceptable salt, and a pharmaceutically acceptable carrier.

11. A method of treating HIV infection in a subject, comprising administering to the subject a therapeutically effective amount of a compound selected from the group consisting of:

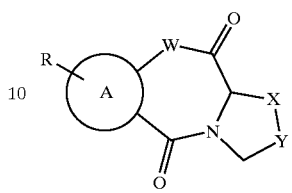 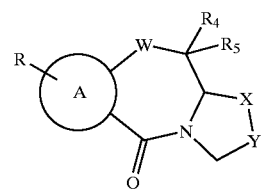

wherein A is benzene or naphthalene;
R is one or more of halogen or $NO_2$;
X—Y is $CH_2$—S, S—$CH_2$, $CH_2$—O, $CH_2$—S(O), S(O)—$CH_2$, $CH_2$—$CH_2$, $CH_2$—$CH_2$—$CH_2$, or $CH_2$—$CH_2$—$CH_2$—$CH_2$;
$R_3$ is H or phenyl;
$R_4$ is H or hydroxy;
$R_5$ is H, phenyl, -alkyl-$NH_2$, —NH-alkyl, or —N(alkyl)$_2$; and
W is S
or wherein the compound is

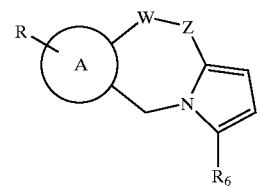

wherein
A is benzene or naphthalene; and
R is one or more of halogen or $NO_2$;
$R_6$ is H, unsubstituted alkyl or amine, or alkyl or amine substituted with at least one substituent selected from halogen, alkyl, alkoxy, alkylthio, trifluoromethyl, acyloxy, hydroxy, mercapto, carboxy, aryloxy, aryl, arylalkyl, amino, alkylamino, dialkylamino, morpholino, piperidino, pyrrolidin-1-yl, or piperazin-1-yl;
W is S; and
Z is S, O, $CH_2$, $CH_2CH_2$, C=O, —$CHCO_2CH_2CH_3$, —$CHC_6H_4$-pF, or —$CHC_6H_5$.

12. A method of treating HIV infection in a subject, comprising administering to the subject a therapeutically effective amount of a compound selected from the group consisting of:

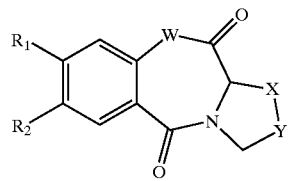

-continued

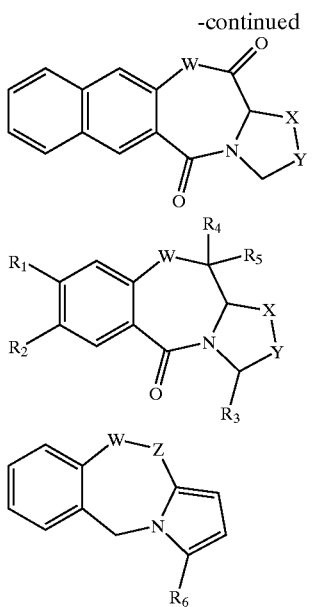

wherein
X—Y is S—CH$_2$, CH$_2$—S, S(O)—CH$_2$, CH$_2$—S(O), or CH$_2$CH$_2$;
Z is S, O, CH$_2$, CH$_2$CH$_2$, C=O, —CHCO$_2$CH$_2$CH$_3$, —CHC$_6$H$_4$-pF, or —CHC$_6$H$_5$;
W is S;
R$_1$ is H, halogen, lower alkyl, lower alkoxy, or NO$_2$;
R$_2$ is H, halogen, lower alkyl or lower alkoxy;
R$_3$ is H;
R$_4$ is hydroxy or H;
R$_5$ is phenyl or N(CH$_2$CH$_2$)$_2$NCH$_3$; and
R$_6$ is CH$_2$N(CH$_2$CH$_2$)$_2$NCH$_3$,
provided that R$_1$ and R$_2$ are not both H or not both alkoxy.

13. The method of claim 12, wherein the compound is

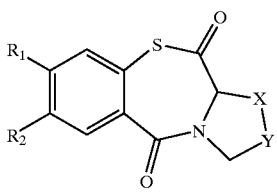

and R$_1$ is H or NO$_2$;
R$_2$ is H, halogen, lower alkyl or lower alkoxy;
provided that R$_1$ and R$_2$ are not both H or not both alkoxy.

14. The method of claim 12, wherein
R$_1$ is H, R$_2$ is Cl, X—Y is S—CH$_2$; or
R is H, R$_2$ is Br, X—Y is S—CH$_2$; or
R$_1$ is H, R$_2$ is CH$_3$, X—Y is S—CH$_2$; or
R$_1$ is H, R$_2$ is Cl, X—Y is CH$_2$—S; or
R$_1$ is H, R$_2$ is Br, X—Y is CH$_2$—S; or
R$_1$ is H, R$_2$ is CH$_3$, X—Y is CH$_2$—S; or
R$_1$ is NO$_2$, R$_2$ is H, X—Y is CH$_2$—S; or
R$_1$ is H, R$_2$ is OCH$_3$, X—Y is CH$_2$—S; or
R$_1$ is H, R$_2$ is CH$_3$, X—Y is S(O)—CH$_2$; or
R$_1$ is H, R$_2$ is Cl, X—Y is CH$_2$—S(O); or
R$_1$ is H, R$_2$ is OCH$_3$, X—Y is CH$_2$—S(O).

15. The method of claim 12, wherein the compound is

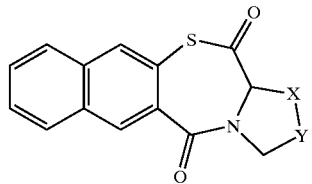

and X—Y is S—CH$_2$ or CH$_2$—S.

16. The method of claim 12, wherein X—Y is S—CH$_2$.

17. A method of treating HIV infection in a subject, comprising administering to the subject a therapeutically effective amount of a compound selected from the group consisting of:

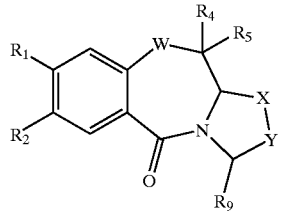

wherein R$_1$, R$_2$ and R$_3$ are H, R$_4$ is OH or H;
W is S;
R$_5$ is Ph or N(CH$_2$CH$_2$)$_2$NCH$_3$; and
X—Y is CH$_2$—CH$_2$.

18. The method of claim 12, wherein the compound is

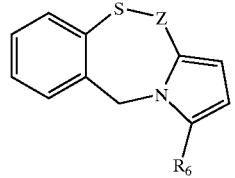

and R$_6$ is CH$_2$N(CH$_2$CH$_2$)$_2$NCH$_3$.

19. A compound having the following formula, or a pharmaceutically acceptable salt thereof, wherein the compound is:

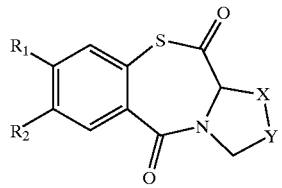

wherein X—Y is S—CH$_2$, CH$_2$—S, S(O)—CH$_2$, or CH$_2$—S(O);
R$_1$ is H or NO$_2$; and
R$_2$ is H, halogen, lower alkyl or lower alkoxy.

20. A method of treating HIV infection in a subject, comprising administering to the subject a therapeutically effective amount of a compound selected from the group consisting of:

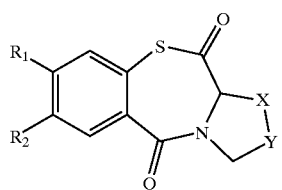
wherein X—Y is S—CH$_2$, CH$_2$—S, S(O)—CH$_2$, or CH$_2$—S(O);
R$_1$ is H or NO$_2$; and
R$_2$ is H, halogen, lower alkyl or lower alkoxy.
21. The compound of claim 5, wherein X—Y is S—CH$_2$.
22. The method of claim 15, wherein X—Y is S—CH$_2$.
* * * * *